United States Patent
Yamanoi et al.

(10) Patent No.: US 10,337,922 B2
(45) Date of Patent: Jul. 2, 2019

(54) COLORIMETER

(71) Applicant: KONICA MINOLTA, INC., Chiyoda-ku (JP)

(72) Inventors: Yuta Yamanoi, Toyonaka (JP); Yasuhisa Kinto, Neyagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/756,472

(22) PCT Filed: Aug. 30, 2016

(86) PCT No.: PCT/JP2016/075332
§ 371 (c)(1),
(2) Date: Feb. 28, 2018

(87) PCT Pub. No.: WO2017/038819
PCT Pub. Date: Mar. 9, 2017

(65) Prior Publication Data
US 2018/0252584 A1    Sep. 6, 2018

(30) Foreign Application Priority Data

Sep. 2, 2015  (JP) ................................. 2015-172975

(51) Int. Cl.
*G01J 3/50* (2006.01)
*G01J 3/02* (2006.01)
(Continued)

(52) U.S. Cl.
CPC ................. *G01J 3/50* (2013.01); *G01J 3/027* (2013.01); *G01J 3/0229* (2013.01);
(Continued)

(58) Field of Classification Search
CPC .... G01J 3/02; G01J 3/50; G01J 3/0229; G01J 3/0251; G01J 3/027; G01J 3/0272;
(Continued)

(56) References Cited

U.S. PATENT DOCUMENTS 5,754,283 A     5/1998   Keane et al.

FOREIGN PATENT DOCUMENTS

JP    2000-505887    5/2000
JP    2001-165938    6/2001
(Continued)

*Primary Examiner* — Jamil Ahmed
(74) *Attorney, Agent, or Firm* — Cozen O'Connor

(57) ABSTRACT

Colorimeter includes an illumination light reception unit, an attached part, a detection unit, a recognition unit, a color measurement control unit, and an output unit. To the attached part, a mask member is attached to cover the illumination light reception unit. The detection unit detects parts disposed on the mask member. The recognition unit recognizes information on the kind of the mask member in accordance with a detection result by the detection unit. The color measurement control unit causes the recognition unit to recognize information on the kind of mask member in accordance with the detection result at a first timing, and on the kind of mask member in accordance with the detection result at a second timing. The output unit performs a predetermined output in response to a discordance between the information on the kind of mask member at the first timing and at the second timing.

18 Claims, 14 Drawing Sheets

(51) Int. Cl.
*G01N 21/25* (2006.01)
*G01J 3/46* (2006.01)

(52) U.S. Cl.
CPC .......... *G01J 3/0251* (2013.01); *G01J 3/0272* (2013.01); *G01J 3/0275* (2013.01); *G01J 3/0291* (2013.01); *G01J 3/46* (2013.01); *G01N 21/251* (2013.01); *G01J 2003/467* (2013.01); *G01N 2201/0221* (2013.01); *G01N 2201/0632* (2013.01)

(58) Field of Classification Search
CPC .......... G01J 3/0275; G01J 3/0291; G01J 3/46; G01J 2003/467; G01N 21/25; G01N 21/251; G01N 2201/0221; G01N 2201/0632
See application file for complete search history.

(56) References Cited

FOREIGN PATENT DOCUMENTS

| | | | |
|---|---|---|---|
| JP | 2003-344552 | 12/2002 | |
| JP | 2004-114343 | 4/2004 | |
| JP | 2006-153498 | 6/2006 | |
| WO | WO 2012/132380 | 10/2012 | |
| WO | WO 2014/061191 | 4/2014 | |
| WO | WO-2014061191 A1 * | 4/2014 | ................ G01J 3/50 |

* cited by examiner

FIG. 13

| ID | MOUNT PATTERN | DETECTION PATTERN IN THE MIDDLE OF ATTACHING | | |
|---|---|---|---|---|
| 1 | 0001 | 1000 | 0100 | 0010 |
| 2 | 0011 | 1000 | 1100 | 0110 |
| 3 | 0101 | 1000 | 0100 | 1010 |
| 4 | 1001 | 1000 | 0100 | 0010 |
| 5 | 1011 | 1000 | 1100 | 0110 |
| 6 | 1101 | 1000 | 0100 | 1010 |
| 7 | 0111 | 1000 | 1100 | 1110 |
| 8 | 1111 | 1000 | 1100 | 1110 |

FIG. 14

| NO. | ID | DETECTION PATTERN | DETERMINATION | REMARKS |
|---|---|---|---|---|
| 1 |  | 0000 | × | ERROR: MASK IS NOT ATTACHED |
| 2 | 1 | 0001 | ○ | FOR 8 mmφ, OPENING WITHOUT PROTECTIVE MEMBER (MAGNET: ABSENT, ABSENT, ABSENT, PRESENT) |
| 3 |  | 0010 | × | ERROR: MASK IS NOT ATTACHED FIRMLY |
| 4 |  | 0100 | × | ERROR: MASK IS NOT ATTACHED FIRMLY |
| 5 |  | 1000 | × | ERROR: MASK IS NOT ATTACHED FIRMLY |
| 6 | 2 | 0011 | ○ | FOR 8 mmφ, OPENING WITH PROTECTIVE GLASS (MAGNET: ABSENT, ABSENT, PRESENT, PRESENT) |
| 7 | 3 | 0101 | ○ | FOR 8 mmφ, OPENING WITH PROTECTIVE PLASTICS (MAGNET: ABSENT, PRESENT, ABSENT, PRESENT) |
| 8 | 4 | 1001 | ○ | FOR 3 mmφ, OPENING WITHOUT PROTECTIVE GLASS (MAGNET: PRESENT, ABSENT, ABSENT, PRESENT) |
| 9 |  | 0110 | × | ERROR: MASK IS NOT ATTACHED FIRMLY |
| 10 |  | 1010 | × | ERROR: MASK IS NOT ATTACHED FIRMLY |
| 11 |  | 1100 | × | ERROR: MASK IS NOT ATTACHED FIRMLY |
| 12 | 5 | 1011 | ○ | CUSTOM MASK 1 (MAGNET: PRESENT, ABSENT, PRESENT, PRESENT) |
| 13 | 6 | 1101 | ○ | CUSTOM MASK 2 (MAGNET: PRESENT, PRESENT, ABSENT, PRESENT) |
| 14 |  | 1110 | × | ERROR: MASK IS NOT ATTACHED FIRMLY |
| 15 | 7 | 0111 | ○ | CUSTOM MASK 3 (MAGNET: ABSENT, PRESENT, PRESENT, PRESENT) |
| 16 | 8 | 1111 | △ | ALERT: FERROMAGNETIC BODY MAY EXIST, ASSUMING THAT STANDARD MASK IS ATTACHED |

FIG. 15

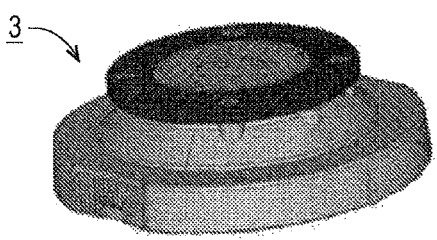

COLORIMETER

RELATED APPLICATIONS

This is a U.S. National Phase Application under 35 USC 371 of International Application PCT/JP2016/075332 filed on Aug. 30, 2016.

This application claims the priority of Japanese application no. 2015-172975 filed Sep. 2, 2015, the entire content of which is hereby incorporated by reference.

TECHNICAL FIELD

The present invention relates to a colorimeter for measuring the color of an object.

BACKGROUND ART

To make various industrial products and the like have constant quality, for example, the products are maintained to have the same color on surfaces thereof. For this purpose, at any stage from the manufacture to the shipment, the color of the surface is measured with a colorimeter or the like to manage the color of the surface. Such a colorimeter includes, for example, an illumination light reception unit including a light source that illuminates a surface of an object whose color is to be measured, such as a product (also referred to as a color measurement object), and a sensor that receives light such as reflection light generated from the surface.

Incidentally, in regard to a part of the surface of the color measurement object whose color is to be managed, that is, a part whose color is to be measured (also referred to as color measurement part), the size and shape may vary depending on various conditions including the shape and size of the color measurement object, the request from clients, the manufacturing method, and the like. However, preparing a different colorimeter for each condition is a large burden on a manufacturer economically.

In view of the above, a portable color measurement device has been suggested (for example, Patent Literature 1) which includes an exchangeable nose cone disposed between a color measurement object and a main body of a colorimeter in accordance with a condition. In this device, for example, the size of a region whose color is to be measured (also referred to as color measurement region) can be changed. This nose cone includes a window part that defines the size of the color measurement region and the like, and is attached to a colorimeter so as to cover the illumination light reception unit, and can function as a member (also referred to as mask member) to be in contact with the color measurement object when the color of the color measurement object is measured.

In such a structure, when the mask member is exchanged, it may be necessary to change an optical system and a calibration coefficient or the like used in the calculation at the color measurement in accordance with the kind of the mask member. In view of this, the device disclosed in Patent Literature 1 includes one or more magnetic switches on a lower half of the main body. The magnetic switch monitors a magnetic field generated from a magnet disposed on the mask member. Thus, the kind of the mask member is automatically recognized and displayed.

CITATION LIST

Patent Literature

Patent Literature 1: JP 2000-505887 A

SUMMARY OF INVENTION

Technical Problem

Incidentally, in a case of managing the color of a product using a colorimeter, for example, the following process is performed: a series of color measurements including measuring of the color of a sample to be a reference (also called a reference sample) and then sequentially measuring the colors of a plurality of samples to be managed and evaluated (also referred to as an evaluation object sample) is performed; and a difference in color between the reference sample and the plurality of evaluation object samples is evaluated. When such a series of color measurements is performed, it is necessary that the condition of the mask member attached to the colorimeter in the color measurement of the reference sample and the condition of the mask member attached to the colorimeter in the color measurement of the plurality of evaluation object samples match.

Although Patent Literature 1 discloses that the kind of the mask member is automatically recognized and displayed, Patent Literature 1 does not discuss whether the mask member in the color measurement of the reference sample and the mask member in the color measurement of the plurality of evaluation object samples match. Therefore, in the technique according to Patent Literature 1, the mask member can be changed arbitrarily by a user in the middle of a series of color measurements. Attaching different mask members to the colorimeter can cause a variation in the color measurement result for the same sample. Therefore, for example, when an operation of changing a mask member is performed in a wrong way in a series of color measurements, a proper evaluation on a difference in color between the reference sample and the evaluation object sample is interrupted.

The present invention has been made in view of the above problem, and it is an object of the present invention to provide a color measurement technique that can properly evaluate a difference in color between the reference sample and the evaluation object sample.

Solution to Problem

In order to achieve the above object, a colorimeter according to one aspect includes an illumination light reception unit, an attached part, a detection unit, a recognition unit, a color measurement control unit, and an output unit. Here, the illumination light reception unit includes a light source unit and a sensor unit. To the attached part, a mask member with a window part is attached so as to cover the illumination light reception unit. The detection unit can detect one or more detected parts disposed on the mask member attached to the attached part. The recognition unit recognizes information on the kind of the mask member in accordance with a detection result of the one or more detected parts by the detection unit. The color measurement control unit causes the recognition unit to recognize the information on the kind of the mask member in accordance with the detection result by the detection unit at a first timing, and causes the recognition unit to recognize the information on the kind of the mask member in accordance with the detection result by the detection unit at a second timing after the first timing. The output unit performs a predetermined output in response to a discordance between the information on the kind of the mask member recognized by the recognition unit in accordance with the detection result by the detection unit at the first timing and the information on the kind of the mask member recognized by the recognition unit in accordance with the detection result by the detection unit at the second timing.

Advantageous Effects of Invention

According to the present invention, a discordance between the mask member in the color measurement of the reference sample and the mask member in the color measurement of the evaluation object sample occurs less; therefore, the difference in color between the reference sample and the evaluation object sample can be evaluated appropriately.

BRIEF DESCRIPTION OF DRAWINGS

FIG. 13 is a diagram illustrating an example of a relation between mount patterns and detection patterns.

FIG. 14 is a diagram illustrating an example of a relation between the detection patterns and determination results.

FIG. 15 is a view illustrating an example of a structure of a mask member.

DESCRIPTION OF EMBODIMENTS

Figure 1:
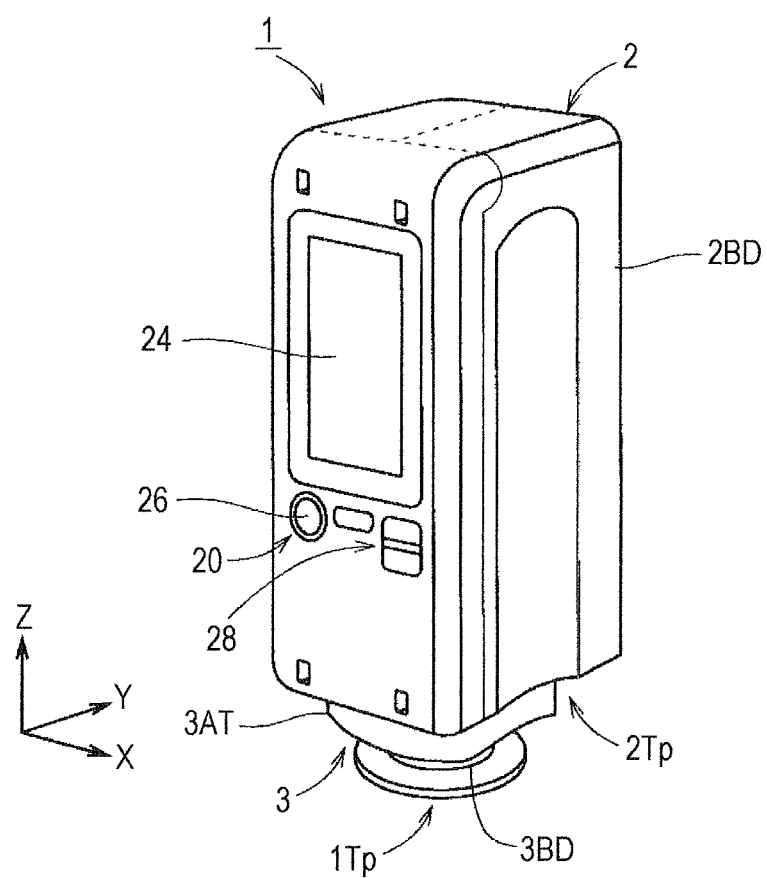
FIG. 1 is a perspective view illustrating an example of an external appearance of a color measurement system according to one embodiment.

One embodiment and various modifications of the present invention will hereinafter be described with reference to the drawings. In the drawings, parts with the similar structure or function are denoted by the same reference signs, and the redundant description will not be made. The drawings are schematic, and the size, the positional relation, and the like of various structures throughout the drawings are changeable. In the right-handed XYZ coordinate system in FIGS. 1 to 6, 10, and 11, a longitudinal direction of a color measurement system 1 (upward direction in FIG. 1) is +Z direction.

(1) One Embodiment

<(1-1) Physical Structure of Color Measurement System>

Figure 2:
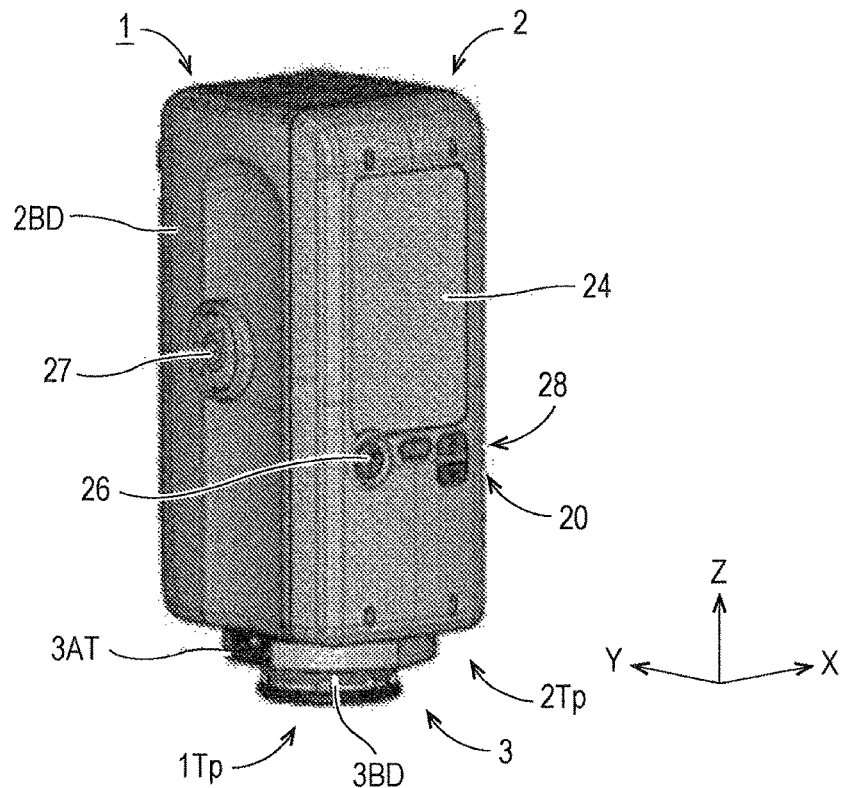
FIG. 2 is a perspective view illustrating an example of the external appearance of the color measurement system according to one embodiment.
Figure 3:
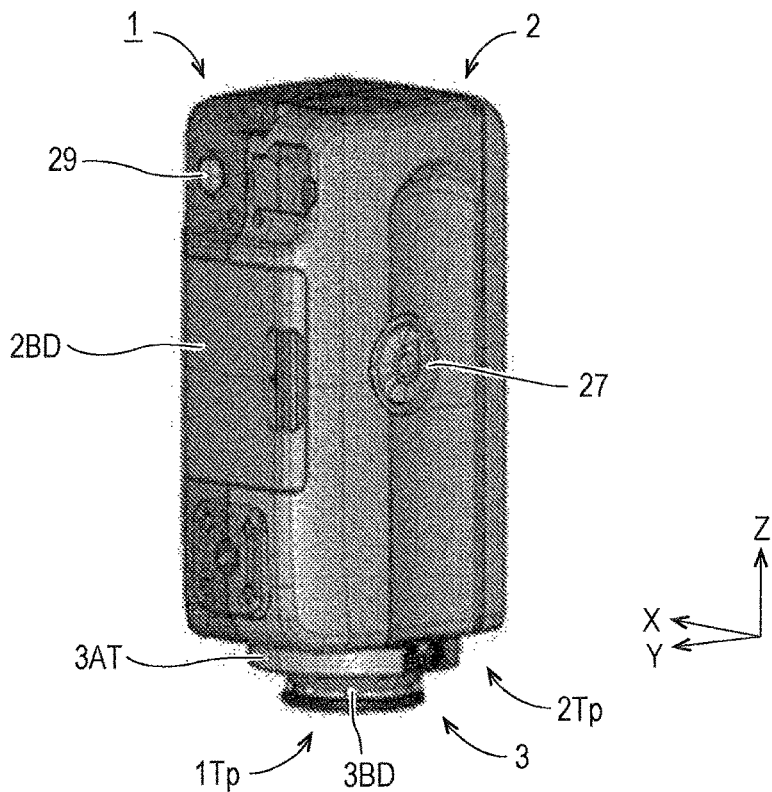
FIG. 3 is a perspective view illustrating an example of the external appearance of the color measurement system according to one embodiment.

FIGS. 1 to 3 are perspective views illustrating an example of an external appearance of the color measurement system 1 according to one embodiment. The color measurement system 1 is an easily carried and relatively compact color measurement system (also referred to as a portable color measurement system). In the color measurement system 1, for example, a color measurement object is irradiated with light, and the light reflected on or transmitted through the color measurement object is spectrally dispersed and received, and then, based on the reflectivity or transmissivity calculated in regard to each wavelength, the color of the color measurement object is calculated.

As illustrated in FIG. 1, the color measurement system 1 includes a colorimeter 2 corresponding to a main body, and a mask member 3 attached to the colorimeter 2.

As illustrated in FIG. 1, the colorimeter 2 includes a casing 2BD, and an input unit 20 and an output unit 24 that are exposed to the outside on a surface of the casing 2BD. The input unit 20 includes first to fourth input units 26 to 29.

The casing 2BD forms an exterior part with an approximately rectangular parallelepiped shape in the color measurement system 1, and includes, for example, a non-magnetic material such as plastic. The casing 2BD includes an upper surface facing +Z direction, a lower surface facing −Z direction, a front surface facing −Y direction, a rear surface facing +Y direction, a first side surface facing +X direction, and a second side surface facing −X direction. As illustrated in FIGS. 1 and 2, the output unit 24 and the first and third input units 26 and 28 are disposed on the front surface of the casing 2BD. In the present embodiment, the output unit 24 includes a display unit that visually outputs various letters, various images, and the like. As illustrated in FIG. 2, the second input unit 27 is disposed on the second side surface of the casing 2BD. As illustrated in FIG. 3, the fourth input unit 29 is disposed in an upper region of the rear surface of the casing 2BD.

The first input unit 26 is, for example, a button (also referred to as a reference button) for setting in order to measure a color of a sample to be a reference (also referred to as a reference sample) when the color of a color measurement object (object color) is measured. The second input unit 27 is, for example, a button (also referred to as a start button) for starting the color measurement for the reference sample and the sample whose object color is to be evaluated (also referred to as the evaluation object sample). The third input unit 28 includes, for example, one or more buttons (also referred to as a specifying button) for specifying various modes or various items. The fourth input unit 29 is, for example, a button (also referred to as a power source button) for supplying power to the colorimeter 2. In FIGS. 1 and 2, the third input unit 28 includes, for example, three buttons of an upper button, a lower button, and a decision button.

Figure 4:
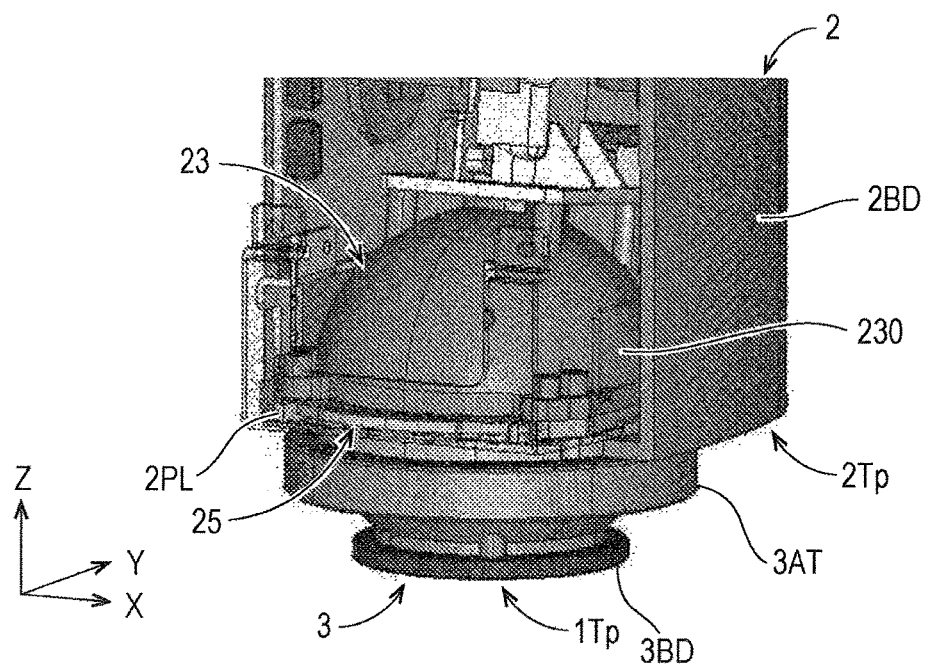
FIG. 4 is a view for describing one structure example around an end part of the color measurement system.
Figure 5:
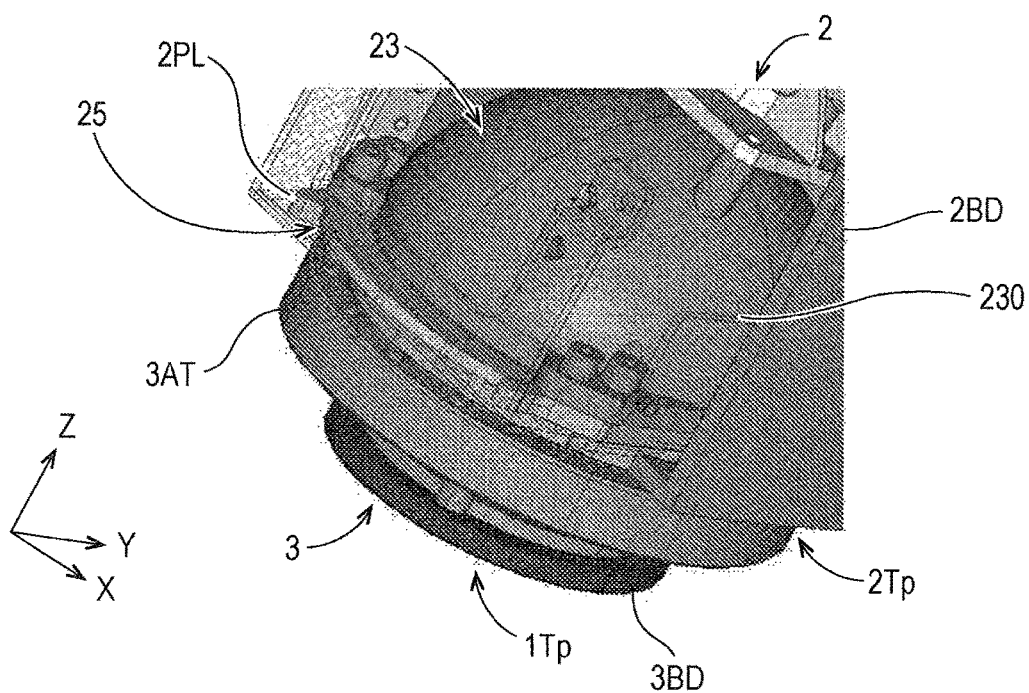
FIG. 5 is a view for describing one structure example around the end part of the color measurement system.
Figure 6:
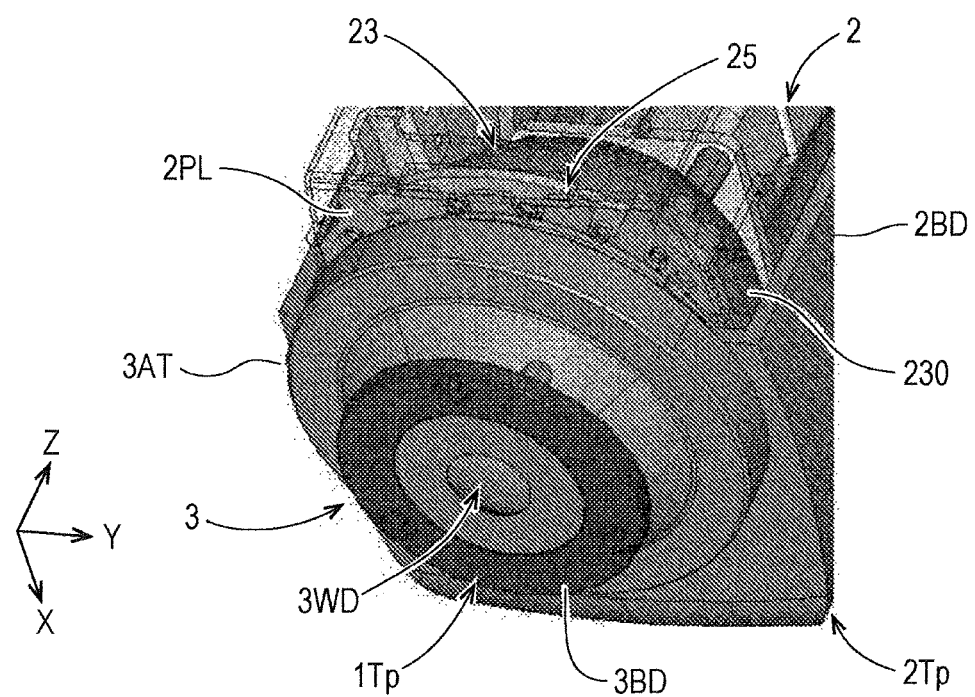
FIG. 6 is a view for describing one structure example around the end part of the color measurement system.

FIGS. 4 to 6 are views illustrating an example of a structure of the color measurement system 1 around an end part 1Tp in −Z direction. Note that in FIGS. 4 to 6, a part of the casing 2BD is transparent for convenience in order to illustrate the structure inside the colorimeter 2.

As illustrated in FIGS. 4 to 6, the colorimeter 2 incorporates a reinforcement member 2PL, an illumination light reception unit 23, and a mask detection unit 25 near an end part 2Tp of the colorimeter 2 in −Z direction. Then, in the color measurement system 1, the mask member 3 is attached to the end part 2Tp of the colorimeter 2 so as to cover the illumination light reception unit 23.

Figure 12:
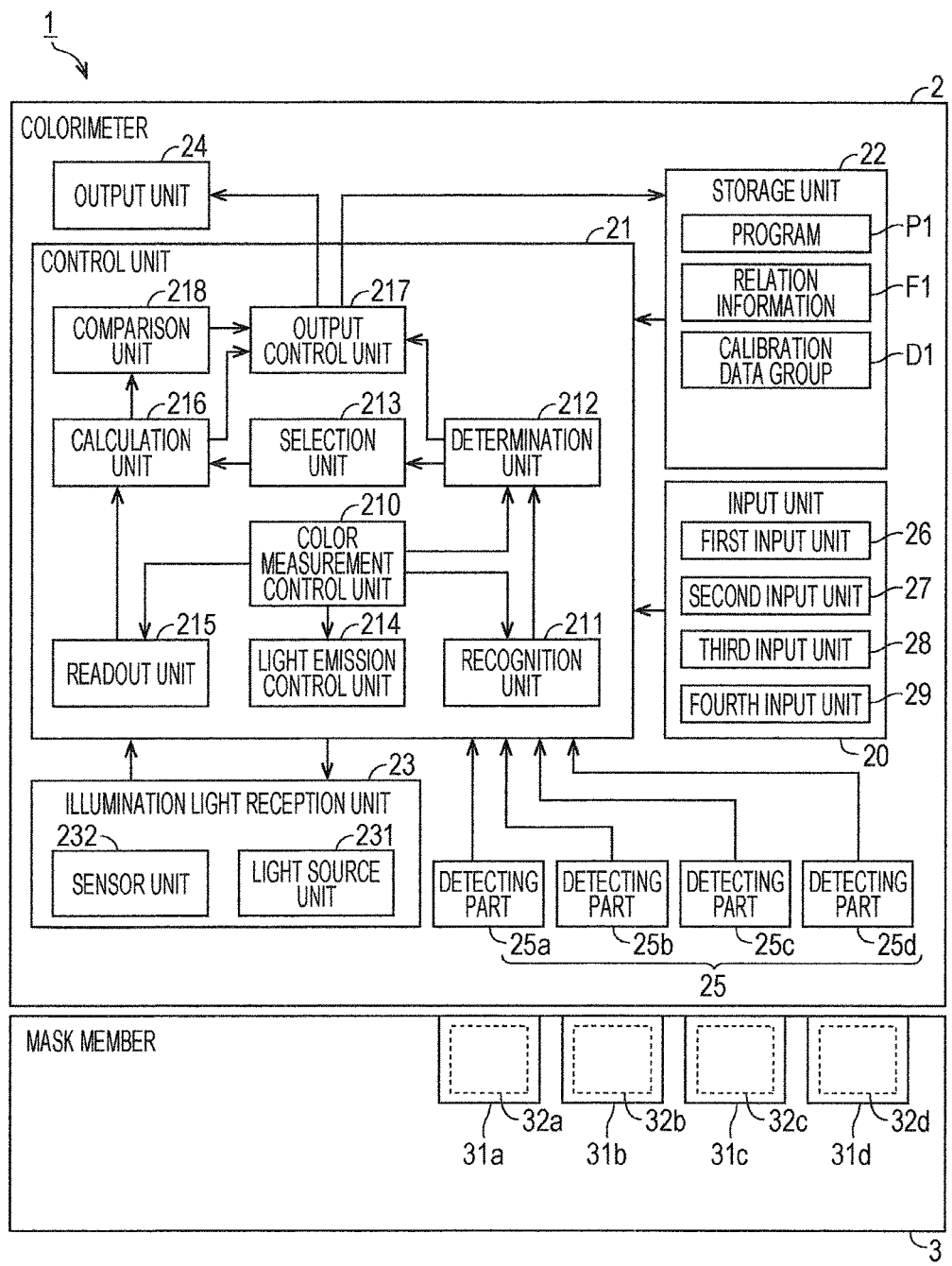
FIG. 12 is a block diagram illustrating an example of functional structures of the color measurement system.

The illumination light reception unit 23 includes an integrating sphere 230, a light source unit 231 (see FIG. 12), and a sensor unit 232 (see FIG. 12).

The integrating sphere 230 is a sphere in which white paint such as barium sulfate for diffusing and reflecting light substantially completely (irregular reflection) is applied on an inner surface.

The light emitted from the light source unit 231 is delivered to a surface of a color measurement object through a window part 2WD (see FIG. 10) communicating with a small window of the integrating sphere 230. This causes the light source unit 231 to illuminate the surface of the color measurement object. Note that the window part 2WD may have, for example, an approximately circular cross-sectional shape along X-Y.

The sensor unit 232 is exposed to the inside of the integrating sphere 230 and the light emitted from the light source unit 231 is not delivered directly to the sensor unit 232. The sensor unit 232 receives the light which is generated from the surface of the color measurement object illuminated with the light source unit 231 and enters the integrating sphere 230. In addition, the sensor unit 232 includes, for example, a spectral unit which spectrally disperses the received light, and a plurality of photoelectric conversion elements each of which receives light with each wavelength emitted from the spectral unit. Thus, from data obtained in the plurality of photoelectric conversion elements of the sensor unit 232, data expressing an object color of a color measurement object corresponding to data of the color measurement result (also referred to as color measurement result data) can be calculated.

The mask detection unit 25 can detect one or more detected parts 32a to 32d (see FIG. 12) disposed on the mask member 3 attached to the end part 2Tp of the colorimeter 2.

The reinforcement member 2PL is a member to secure the rigidity of the end part 2Tp of the colorimeter 2. The reinforcement member 2PL is, for example, a plate-shaped member formed of a material with high rigidity, such as iron. Since an outer periphery of the integrating sphere 230 is protected with the reinforcement 2PL, the damage of the integrating sphere 230 can be prevented. In addition, the reinforcement member 2PL holds the mask detection unit 25. This can protect and fix the mask detection unit 25. In the colorimeter 2, the casing 2BD forming the exterior part is disposed outside the reinforcement member 2PL.

The mask member 3 is a member that is attached to the end part 2Tp of the colorimeter 2 so as to cover the illumination light reception unit 23 and that is brought into contact with the color measurement object when the color of the color measurement object is measured. The mask member 3 includes a main body 3BD and an attaching part 3AT. The main body 3BD includes a window part 3WD that defines the size of a region of the color measurement object whose color is to be measured (also referred to as a color measurement region). The window part 3WD may have, for example, an approximately circular cross-sectional shape along X-Y. The window part 3WD communicates with the window part 2WD of the colorimeter 2 and the small window of the integrating sphere 230 in a state that the mask member 3 is attached to the end part 2Tp of the colorimeter 2. The attaching part 3AT is a part where the mask member 3 is attached to the colorimeter 2. The mask member 3 is also referred to as a target mask or the like, for example.

Figure 7:
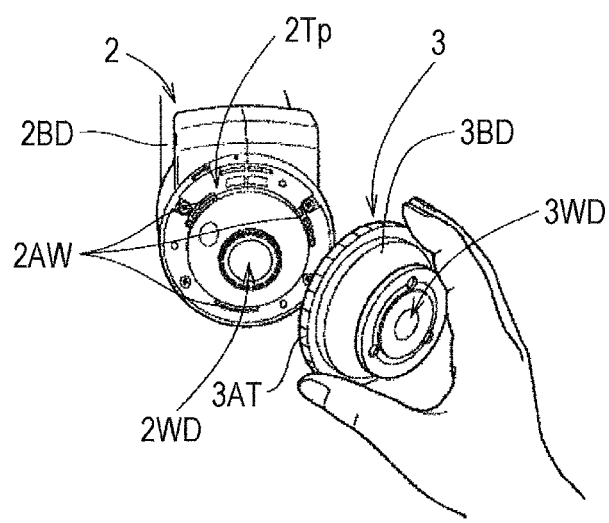
FIG. 7 is a view illustrating that a mask member is detachable relative to a colorimeter.
Figure 8:
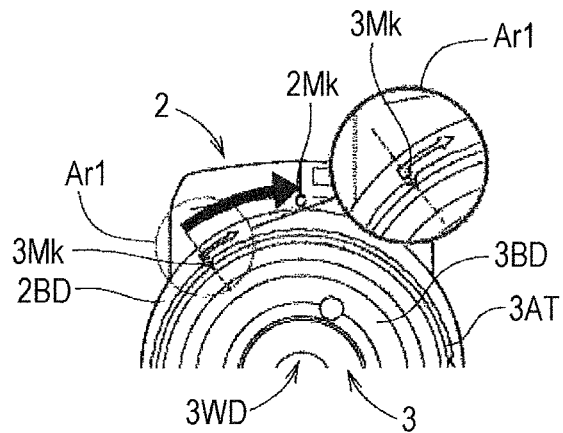
FIG. 8 is a view illustrating that a mask member is detachable relative to the colorimeter.
Figure 9:
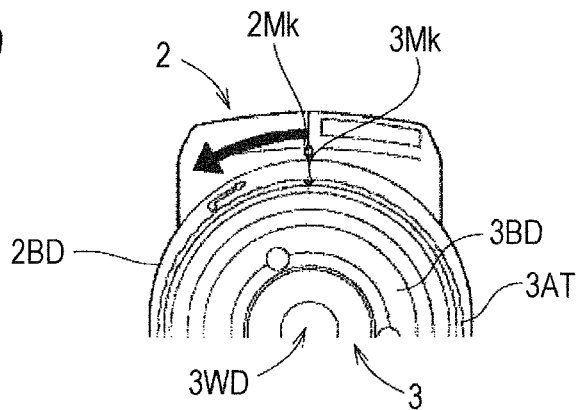
FIG. 9 is a view illustrating that a mask member is detachable relative to the colorimeter.

The mask member 3 can be attached to or detached from the end part 2Tp of the colorimeter 2. In FIGS. 7 to 9, the mask member 3 is detachable relative to the colorimeter 2.

As illustrated in FIG. 7, an attached part 2AW to which the mask member 3 is attached so that the mask member 3 covers the illumination light reception unit 23 is provided at the end part 2Tp of the colorimeter 2. The attached part 2AW constitutes a part of the casing 2BD. Specifically, for example, by attaching the attaching part 3AT to the attached part 2AW, the mask member 3 is attached to the colorimeter 2.

In the present embodiment, as a mechanism including the attached part 2AW and the attaching part 3AT (also referred to as an attachment mechanism), for example, an attachment mechanism called a bayonet type in which the attaching part 3AT is attached to the attached part 2AW by rotating the attaching part 3AT relative to the attached part 2AW is employed. In this mechanism, for example, the attaching part 3AT is fixed to the attached part 2AW by rotating the mask member 3 around an axis passing a center of the window parts 2WD and 3WD in a state that a plurality of claw parts provided to the attaching part 3AT is caught by a stopper of the attached part 2AW. The number of claw parts may be, for example, three.

FIG. 8 illustrates a state in which the attaching part 3AT starts to be attached to the attached part 2AW, and FIG. 9 illustrates a state in which the attachment of the attaching part 3AT to the attached part 2AW is completed. Note that in FIG. 8, a region Ar1 surrounded by a round frame is magnified. As illustrated in FIG. 8, by rotating the mask member 3 in a direction indicated by a black arrow, the mask member 3 is attached to a position on the attached part 2AW that is set in advance to perform the color measurement (this position is also referred to as an attachment position).

For example, as illustrated in FIG. 8, first, the mask member 3 is pressed against the end part 2Tp so that a cut part 3Mk as a mark provided to an outer periphery of the mask member 3 is aligned to a start end part of a white arrow corresponding to a mark drawn at the end part 2Tp. Then, while the mask member 3 is pressed against the end part 2Tp, the mask member 3 is rotated by a predetermined angle (for example, about 30°) in a clockwise direction relative to the end part 2Tp, so that the attaching part 3AT of the mask member 3 is attached to the attached part 2AW of the colorimeter 2. The clockwise direction herein described refers to the clockwise direction when the mask member 3 is seen in plan view in +Z direction.

Here, at this time, for example, the cut part 3Mk is aligned to a round mark 2Mk as the mark drawn at the end part 2Tp of the colorimeter 2 as illustrated in FIG. 9. Note that, at this time, for example, the attached part 2AW and the attaching part 3AT may be fixed to each other in a state that those parts are engaged with each other or anchored with each other, by rotating the attaching part 3AT in the clockwise direction with a force of a certain degree or more. Thus, the attachment of the mask member 3 to the colorimeter 2 is completed.

On the other hand, as illustrated in FIG. 9, by rotating the mask member 3 by a predetermined angle in a counterclockwise direction as drawn by a black arrow, which is a direction opposite to the direction where the mask member 3 is attached to the colorimeter 2, the mask member 3 is detached from the colorimeter 2. The counterclockwise direction herein described refers to the counterclockwise direction when the mask member 3 is seen in plan view in +Z direction. Note that, at this time, for example, the engagement or anchoring between the attached part 2AW and the attaching part 3AT may be canceled by rotating the attaching part 3AT in the counterclockwise direction with a force of a certain degree or more.

Figure 10:
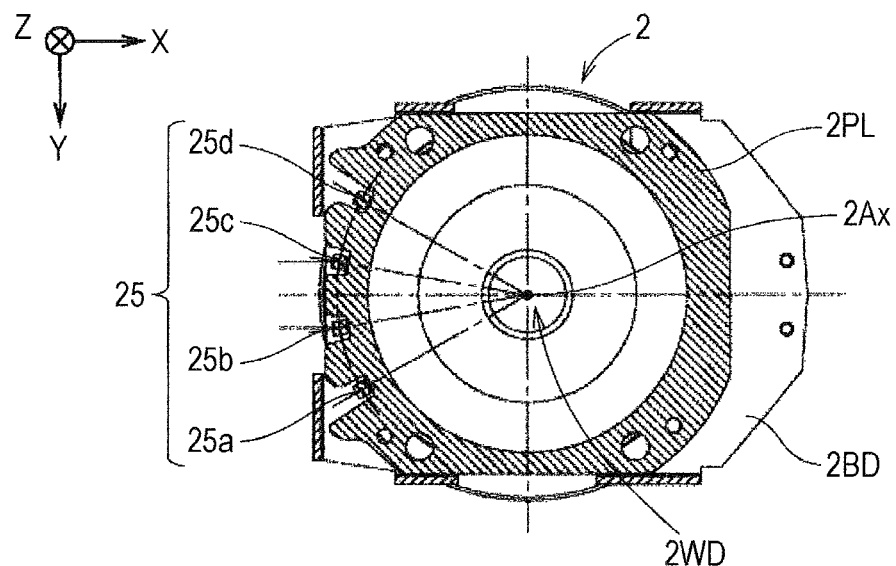
FIG. 10 is a view for describing a structure of a mask detection unit.

FIG. 10 is a view illustrating an example of a structure of the mask detection unit 25 disposed near the end part 2Tp of the colorimeter 2. In FIG. 10, the casing 2BD including the attached part 2AW is illustrated as being transparent for the convenience in order to illustrate the structure of the mask detection unit 25.

As illustrated in FIG. 10, the mask detection unit 25 includes a plurality of detecting parts 25a to 25d. The detecting parts 25a to 25d can detect the detected parts 32a to 32d (see FIG. 12) disposed on the mask member 3. That is to say, the mask detection unit 25 can detect one or more detected parts 32a to 32d disposed on the mask member 3 attached to the attached part 2AW. In the present embodiment, a Hall element is employed as the detecting parts 25a to 25d, and a magnet is employed as the detected parts 32a to 32d. The Hall element can detect a magnet by detecting the magnetic field generated from the magnet.

In addition, as illustrated in FIG. 10, in the present embodiment, the plurality of detecting parts 25a to 25d is disposed in a portion where the reinforcement member 2PL is not disposed when the end part 2Tp of the colorimeter 2 is seen through in plan view in +Z direction. Specifically, for example, a plurality of cut parts is provided to the reinforcement member 2PL, and the detecting parts 25a to 25d are disposed at the cut parts. This makes it difficult for the reinforcement member 2PL to interrupt the detection of the mask member 3 by the mask detection unit 25.

The plurality of detecting parts 25a to 25d is disposed in a direction where the mask member 3 is moved relative to the attached part 2AW (also referred to as attaching direction) in the middle of attaching the mask member 3 to the attached part 2AW. In the present embodiment, the attaching direction is the clockwise direction around an axis 2Ax passing the substantial center of the window part 2WD. The clockwise direction described here refers to the clockwise direction when the end part 2Tp is seen in plan view in +Z direction. The plurality of detecting parts 25a to 25d is arranged in this order in the clockwise direction corresponding to the attaching direction. As illustrated in FIG. 10, the adjacent detecting parts among the plurality of detecting parts 25a to 25d are disposed at substantially equal intervals along the attaching direction, for example.

Figure 11:
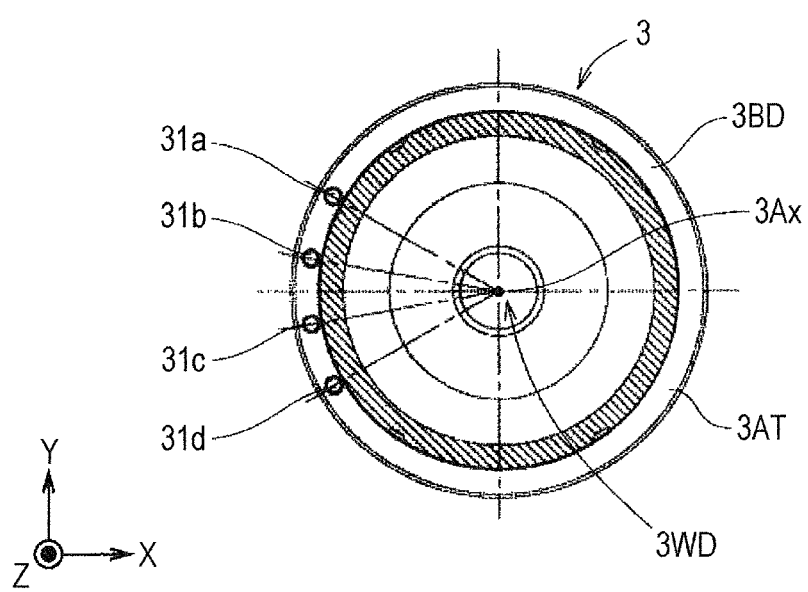
FIG. 11 is a view illustrating an example of a structure of the mask member.

FIG. 11 is a view illustrating one structure example of the mask member 3. FIG. 11 illustrates a surface of the mask member 3 that is positioned on the colorimeter 2 side when the mask member 3 is attached to the colorimeter 2.

As illustrated in FIG. 11, the mask member 3 is provided with a plurality of mounted parts 31a to 31d where the detected parts 32a to 32d can be mounted, and the mounted parts 31a to 31d are provided near an outer periphery of the mask member 3. In the present embodiment, the mounted parts 31a to 31d are concavities. The plurality of mounted parts 31a to 31d is arranged along the attaching direction where the mask member 3 is moved relative to the attached part 2AW in the middle of attaching the mask member 3 to the attached part 2AW. In FIG. 11, the attaching direction is the counterclockwise direction around an axis 3Ax passing the substantial center of the window part 3WD when the mask member 3 is seen in plan view in −Z direction. The plurality of mounted parts 31a to 31d is arranged in this order in the attaching direction. As illustrated in FIG. 11, the adjacent mounted parts among the plurality of mounted parts 31a to 31d are set, for example, at substantially equal intervals along the attaching direction.

Here, when the attachment of the mask member 3 to the predetermined attachment position on the attached part 2AW for performing the color measurement is completed (this state is referred to as an attachment completed state), the plurality of mounted parts 31a to 31d faces the plurality of detecting parts 25a to 25d in +Z direction. Specifically, the mounted part 31a faces the detecting part 25a, the mounted part 31b faces the detecting part 25b, the mounted part 31c faces the detecting part 25c, and the mounted part 31d faces the detecting part 25d.

A pattern expressing whether the detected parts 32a to 32d are mounted on the plurality of mounted parts 31a to 31d (also referred to as the mount pattern) is changed depending on the kind of the mask member 3. Thus, a pattern of detection (also referred to as a detection pattern) of the detected parts 32a to 32d in accordance with the kind of the mask member 3 can be achieved by the plurality of detecting parts 25a to 25d.

<(1-2) Functional Structure of Color Measurement System>

FIG. 12 is a block diagram illustrating an example of functional structures of the color measurement system 1.

As illustrated in FIG. 12, the colorimeter 2 includes the input unit 20, a control unit 21, a storage unit 22, the illumination light reception unit 23, the output unit 24, and the mask detection unit 25. The mask member 3 includes a plurality of mounted parts 31a to 31d, and to each of the mounted parts 31a to 31d, each of the detected parts 32a to 32d is mounted in accordance with the kind of the mask member 3.

The input unit 20 outputs, to the control unit 21, a signal in accordance with the operation of the user. For example, the input unit 20 includes a reference button as the first input unit 26, a specifying button as the second input unit 27, a measurement button as the third input unit 28, a power source button as the fourth input unit 29, and the like. The functions of the first input unit 26 to the third input unit 28 may be achieved by, for example a touch panel configured integrally with a display unit as the output unit 24. Furthermore, for example, the first input unit 26 to the third input unit 28 may have a function of inputting, in response to a voice generated from a user, a signal according to the voice.

The storage unit 22 is configured by a nonvolatile storage medium or the like, and stores, for example, a program P1, relation information F1, and a calibration data group D1. The program P1, the relation information F1, and the calibration data group D1 can be stored in the storage unit 22 at a timing of, for example, any stage from the manufacture to the shipment of the colorimeter 2.

The program P1 is to achieve each function of the control unit 21 when the program P1 is read and executed by a processor in the control unit 21.

The relation information F1 includes the information expressing the relation between the detection pattern and the information that specifies the kind of the mask member 3 (such as the name and the identification information). The identification information may include, for example, a serial number.

The calibration data group D1 includes, for example, a plurality of pieces of calibration data in accordance with the kind of the mask member 3. Each piece of calibration data is used in the calculation (also referred to as colorimetric calculation) to obtain the data pertaining to the color of the color measurement object (such as the object color) as the color measurement result data on the basis of the data obtained by the sensor unit 232.

The illumination light reception unit 23 includes the light source unit 231 and the sensor unit 232 as described above. The light source unit 231 emits light under the control of the light emission control unit 214 of the control unit 21. The sensor unit 232 obtains an electric signal according to the intensity of the received light. The signal is read out by a readout unit 215.

The output unit 24 includes, for example, a display unit such as a liquid crystal display, and visually outputs various kinds of information under the control of an output control unit 217 of the control unit 21.

The mask detection unit 25 includes the plurality of detecting parts 25a to 25d as described above. The detecting parts 25a to 25d detect the detected parts 32a to 32d mounted on the mounted parts 31a to 31d. For example, in the case where each of the detecting parts 25a to 25d includes a Hall element and each of the detected parts 32a to 32d includes a magnet, each of the detecting parts 25a to 25d outputs an electromagnetic force (signal) according to the magnetic field generated from the detected parts 32a to 32d to the control unit 21.

The control unit 21 includes a central processing unit (CPU) as a processor, a volatile memory, and the like, and achieves various functions by reading and executing the program P1 stored in the storage unit 22. The structures functionally achieved by the control unit 21 include, for example, a color measurement control unit 210, a recognition unit 211, a determination unit 212, a selection unit 213, the light emission control unit 214, the readout unit 215, a calculation unit 216, the output control unit 217, and a comparison unit 218.

The recognition unit 211 recognizes information on the kind of the mask member 3 in accordance with the detection result of one or more of the detected parts 32a to 32d by the mask detection unit 25. Here, the information on the kind of the mask member 3 may include the name and the identification information of the mask member 3 that specify the kind of the mask member 3, the detection pattern of the detected parts 32a to 32d, and the like. For example, the recognition unit 211 recognizes the detecting part among the plurality of detecting parts 25a to 25d that detects the detected parts 32a to 32d, and thus, the detection pattern corresponding to the combination of two or more detecting parts among the plurality of detecting parts 25a to 25d that detects the detected parts 32a to 32d can be recognized. In another example, the recognition unit 211 can recognize the name and the identification information of the mask member 3 corresponding to the recognized detection pattern on the basis of the relation information F1 expressing the relation between the detection pattern, and the name and the identification information of the mask member 3.

The determination unit 212 determines whether the information on the kind of the mask member 3 recognized by the recognition unit 211 in accordance with the detection result by the mask detection unit 25 at a first timing and the information on the kind of the mask member 3 recognized by the recognition unit 211 in accordance with the detection result by the mask detection unit 25 at a second timing match.

Here, the first timing is a timing of the color measurement in which the color measurement object is a first sample, and the second timing is a timing of the color measurement in which the color measurement object is a second sample. For example, the first timing is a timing at which the colorimeter 2 is set to a mode of measuring a color of a reference sample as the first sample corresponding to a reference (also referred to as a reference mode). For example, by pressing a power source button or a reference button, the colorimeter 2 can be set to the reference mode. In addition, for example, the second timing is a timing at which the colorimeter 2 is set to a mode (also referred to as a color measurement mode) of measuring a color of a sample to be subjected to the color measurement, which is different from the reference sample (also referred to as a color measurement object sample). In the present embodiment, the color measurement object sample corresponds to an evaluation object sample. For example, the colorimeter 2 can be set to a color measurement mode immediately after, or after a predetermined period from, the end of the color measurement in the reference mode. The first timing includes, for example, at least one timing of the following: before the color measurement, in the middle of the color measurement, and after the color measurement of the first sample. The second timing includes, for example, at least one timing of the following: before the color measurement, in the middle of the color measurement, and after the color measurement of the second sample that is different from the first sample.

For example, when the color and the like of a product are managed by using the colorimeter 2, the first sample includes the reference sample to be a reference. The second sample includes, for example, an evaluation object sample as an object whose color difference based on the reference sample is evaluated. In these cases, at the first timing, the color measurement in which the color measurement object is the reference sample is performed (also referred to as color measurement for reference), and at the second timing, the color measurement in which the color measurement object is the evaluation object sample is performed (also referred to as color measurement for evaluation).

The selection unit 213 selects the calibration data corresponding to the information on the kind of the mask member 3 identified by the recognition unit 211, from among the calibration data group D1 stored in the storage unit 22. The calibration data selected in the selection unit 213 are used in the color measurement calculation in the calculation unit 216.

The light emission control unit 214 controls the light emission in the light source unit 231 in response to, for example, the user's operation on the measurement button corresponding to the second input unit 27.

The readout unit 215 reads out charges, which are obtained in accordance with the light reception in the sensor unit 232, at an appropriate timing and outputs the charges to the calculation unit 216. This causes the sensor unit 232 to output an analog signal. When the sensor unit 232 includes a unit (also referred to as an A/D converter) that converts an analog signal to a digital signal (also referred to as A/D conversion process), the readout unit 215 can output the data obtained from the sensor unit 232 directly to the calculation unit 216. If the sensor unit 232 does not have the A/D converter, the readout unit 215 may perform the A/D conversion process.

The calculation unit 216 obtains the color measurement result data pertaining to the object color of the color measurement object on the basis of the electric signal obtained in the illumination light reception unit 23 when the light from the light source unit 231 is delivered to the color measurement object and the light generated from the color measurement object is received in the sensor unit 232. Specifically, from the data obtained in the sensor unit 232 and input through the readout unit 215, the calculation unit 216 performs the color measurement calculation to calculate the data pertaining to the object color of the color measurement object as the color measurement result data. Here, the calculation unit 216 performs the color measurement calculation using the calibration data corresponding to the information on the kind of the mask member 3 recognized by the recognition unit 211 among the calibration data group D1 stored in the storage unit 22. Thus, the change of the calibration data in accordance with the kind of the mask member 3 can be achieved easily and correctly. In the present embodiment, the calibration data can be selected by the selection unit 213. In addition, the color measurement result data obtained in the calculation unit 216 are stored in the storage unit 22 as appropriate.

The color measurement control unit 210 causes the recognition unit 211 to recognize the information on the kind of the mask member 3 on the basis of the detection result by the mask detection unit 25 at the first timing, and causes the recognition unit 211 to recognize the information on the kind of the mask member 3 on the basis of the detection result by the mask detection unit 25 at the second timing after the first timing.

The output control unit 217 controls the output of the output unit 24 and moreover controls the storage of the data in the storage unit 22. Here, in response to a discordance between the information on the kind of the mask member recognized by the recognition unit 211 on the basis of the detection result by the mask detection unit 25 at the first timing and the information on the kind of the mask member 3 recognized by the recognition unit 211 on the basis of the detection result by the mask detection unit 25 at the second timing, the output unit 24 performs a predetermined output by the control of the output control unit 217, for example.

In the example described in the present embodiment, the output unit 24 is a display unit that performs a predetermined visible output; however, the present invention is not limited to this example. For example, the output unit 24 may include at least one of the following units that perform output in response to a discordance of the kind of the mask member 3: a display unit that performs a predetermined visible output, a light-emitting unit that performs predetermined light emission, a projection unit that performs a predetermined visible output, a speaker unit that performs a predetermined audible output, and a communication unit that outputs a predetermined signal. In other words, for example, the output unit 24 may perform an output in a predetermined mode that a user can recognize, in response to the discordance of the information on the kind of the mask member 3. By the output in any of these modes, the user can be easily notified of the discordance of the kind of the mask member between when the color of the reference sample is measured (color measurement for reference) and when the color of the evaluation object sample is measured (color measurement for evaluation).

The comparison unit 218 compares the color measurement result of the color measurement for reference with the color measurement result of the color measurement for evaluation. For example, the difference (also referred to as color difference) between the color measurement result of the color measurement for reference, and the color measurement result of the color measurement for evaluation is calculated. The data on the color difference calculated here are subjected to at least one of the output from the output unit 24 by the control of the output control unit 217, and the storage into the storage unit 22 by the control of the output control unit 217.

<(1-3) Pattern of Color Measurement Operation>

A pattern of a series of color measurement operations to compare the color measurement result with the subsequent color measurement for evaluation based on the color measurement result of the color measurement for reference is, for example, a first pattern and a second pattern as below.

<(1-3-1) First Pattern>

In the first pattern, the process of next steps [A1] to [A5] is performed in order.

[A1] A power source button as the fourth input unit 29 is pressed to turn on the power source of the colorimeter 2.

[A2] The mask member 3 of the color measurement system 1 is pressed against the reference sample, and the measurement button as the second input unit 27 is pressed; thus, the color measurement for reference is performed. The color measurement result data obtained here are, for example, output visually on the output unit 24 and stored in the storage unit 22.

[A3] The mask member 3 of the color measurement system 1 is pressed against the first evaluation object sample, and the measurement button as the second input unit 27 is pressed; thus, the color measurement for evaluation is performed. The color difference corresponding to the result of comparing between the color measurement result data of the color measurement for evaluation obtained here and the color measurement result data of the color measurement for reference obtained in step [A2] is, for example, visually output on the output unit 24 and stored in the storage unit 22.

[A4] The mask member 3 of the color measurement system 1 is pressed against the second evaluation object sample, and the measurement button as the second input unit 27 is pressed; thus, the color measurement for evaluation is performed. The color difference corresponding to the result of comparing between the color measurement result data of the color measurement for evaluation obtained here and the color measurement result data of the color measurement for reference obtained in step [A2] is, for example, visually output on the output unit 24 and stored in the storage unit 22.

[A5] After that, the color measurement for evaluation is performed in order in regard to the N-th (N is a natural number of 3 or more) evaluation object sample. Then, for each color measurement for evaluation, the color difference corresponding to the result of comparing between the color measurement result data of the color measurement for evaluation and the color measurement result data of the color measurement for reference obtained in step [A2] is, for example, visually output on the output unit 24 and stored in the storage unit 22.

<(1-3-2) Second Pattern>

In the second pattern, the process in next steps [B1] to [B6] is performed in order.

[B1] The power source button as the fourth input unit 29 is pressed to turn on the power source of the colorimeter 2.

[B2] The mask member 3 of the color measurement system 1 is pressed against the first reference sample, and the measurement button as the second input unit 27 is pressed; thus, the color measurement for reference is performed. The color measurement result data obtained here are, for example, visually output on the output unit 24 and stored in the storage unit 22.

[B3] After that, the color measurement for evaluation is performed in order in regard to the M (M is a natural number) evaluation object samples. Then, for each color measurement for evaluation, the color difference corresponding to the result of comparing between the color measurement result data of the color measurement for evaluation and the color measurement result data of the color measurement for reference obtained in step [B2] is, for example, visually output on the output unit 24 and stored in the storage unit 22.

[B4] The reference button as the first input unit 26 is pressed.

[B5] The mask member 3 of the color measurement system 1 is pressed against the second reference sample, and the measurement button as the second input unit 27 is pressed; thus, the color measurement for reference is performed. The color measurement result data obtained here are, for example, visually output on the output unit 24 and stored in the storage unit 22.

[B6] After that, the color measurement for evaluation is performed in order in regard to the m (m is a natural number) evaluation object samples. Then, for each color measurement for evaluation, the color difference corresponding to the result of comparing between the color measurement result data of the color measurement for evaluation and the color measurement result data of the color measurement for reference obtained in step [B5] is, for example, visually output on the output unit 24 and stored in the storage unit 22.

<(1-4) Mount Pattern and Detection Pattern>

In the color measurement system 1 according to the present embodiment, the recognition unit 211 recognizes, for example, the detection pattern corresponding to the combination of two or more detecting parts among the plurality of detecting parts 25a to 25d that detect the detected parts 32a to 32d.

For example, the detecting part 25d, which is positioned deepest in the attaching direction among the plurality of detecting parts 25a to 25d, detects the detected part 32d when the attaching of the mask member 3 at the attaching position is completed. In this case, among the plurality of mounted parts 31a to 31d, the detected part 32d is mounted on the mounted part 31d that is positioned at the head in the attaching direction. Thus, the wrong detection that does not express the kind of the mask member 3 in the state that the mount of the mask member 3 is not completed yet can be reduced.

FIG. 13 is a diagram illustrating the mount patterns and the detection patterns in the middle of attaching in the case where the detected part 32d is mounted on the mounted part 31d.

In FIG. 13, whether the detected parts 32a to 32d are mounted on the mounted parts 31a to 31d is expressed by "0" or "1", and the mount pattern in the mounted parts 31a to 31d is expressed in a set of four-digit number. This set of four-digit number expresses, in the order from left, whether the detected part 32a is mounted on the mounted part 31a, the detected part 32b is mounted on the mounted part 31b, the detected part 32c is mounted on the mounted part 31c, and the detected part 32d is mounted on the mounted part 31d. For example, the mount pattern "0001" expresses that only on the mounted part 31d among the four mounted parts 31a to 31d, the detected part 32d is mounted.

In FIG. 13, whether the detected parts 32a to 32d are detected by the detecting parts 25a to 25d in the middle of attaching is expressed by "0" or "1", and the detection pattern by the detecting parts 25a to 25d is expressed by a set of four-digit number. This set of four-digit number expresses, in the order from left, whether the detection is performed by the detecting part 25a, the detection is performed by the detecting part 25b, the detection is performed by the detecting part 25c, and the detection is performed by the detecting part 25d. For example, the detection pattern "1000" expresses that only the detecting part 25a among the four detecting parts 25a to 25d has detected any of the detected parts 32a to 32d. Since the detection pattern in the attaching completed state is the same as the mount pattern, FIG. 13 illustrates the detection pattern in the middle of attaching in regard to each mount pattern.

As illustrated in FIG. 13, in the eight mount patterns provided with the identification information (ID) 1 to 8, the detection patterns in the middle of attaching may overlap between the different mount patterns. Specifically, seven detection patterns of "1000", "1010", "1100", "1110", "0100", "0110", and "0010" can be recognized a plurality of times. Therefore, when these seven detection patterns are recognized, it is impossible to determine whether the mask member 3 is in the middle of attaching, or the mask member 3 having employed the mount pattern for the seven detection patterns are not attached yet. That is to say, the wrong detection state that does not express the kind of the mask member 3 can be recognized.

In view of this, eight mount patterns are employed for eight kinds of mask members 3, and the eight detection patterns recognized when the detected part 32d is detected by the detecting part 25d among the plurality of detecting parts 25a to 25d is associated with those eight mount patterns. This can avoid the recognition of the wrong detection state that does not express the kind of the mask member 3.

FIG. 14 is a diagram illustrating an example of the content of the relation information F1 expressing the relation between the detection patterns and the kind of the mask member 3 in the case where the eight mount patterns with the IDs 1 to 8 are employed. As expressed in FIG. 14, in the relation information F1, various kinds of mask members 3 are associated with the eight detection patterns recognized when the detected part 32d is detected by the detecting part 25d. The eight detection patterns are detection patterns for the eight mount patterns with the IDs 1 to 8. In FIG. 14, a cross mark is illustrated as the determination result for the detection pattern with which the mask member 3 is not associated among the detection patterns.

Here, the detection pattern "0000" is the same as the detection pattern in the state where the mask member 3 is not attached to the colorimeter 2; therefore, the mask member 3 is not associated. The detection pattern "1111" is the same detection pattern as that in the state in which the object emitting a ferromagnetic field is disposed near the detecting parts 25a to 25d; therefore, it may be unnecessary that the mask member 3 is associated. However, in the present embodiment, the standard mask member 3 is associated with the detection pattern "1111" and a triangular mark is illustrated as the determination result.

Incidentally, as expressed by FIGS. 13 and 14, only one detected part 32d is mounted to the mask member 3 in the mount pattern with the ID 1, and in the mount patterns with the other IDs, two or more detected parts 32a to 32d are mounted to the mask member 3. That is to say, the mask member 3 includes two or more detected parts 32a to 32d, which can be detected by the detecting parts 25a to 25d, respectively, along the attaching direction where the mask member 3 is moved relative to the attached part 2AW in the middle of attaching to the attached part 2AW. Thus, the proper detection state in accordance with the kind of the mask member 3 attached to the colorimeter 2 can be achieved in the colorimeter 2.

<(1-5) Variation of Mask Member>

There is a plurality of kinds of mask members 3 to be in contact with various measurement objects.

The mask member 3 includes the window part 3WD with a circular opening, and this opening is protected with a material (also referred to as an opening protective material), such as glass or plastic. Here, since the transmissivity of visible light through glass and the transmissivity of visible light through plastic are different, it is necessary to distinguish between the mask member 3 whose opening protective material is glass and the mask member 3 whose opening protective material is plastic. When the measurement object is a food, for example, the mask member 3 whose opening protective material is glass may not be used. In this case, it is also necessary to distinguish between the mask member 3 whose opening protective material is glass and the mask member 3 whose opening protective material is plastic. However, plastic is disadvantageous in, for example, the durability and the transmissivity of ultraviolet light. The mask member 3 not having the opening protective material may have an opening with a different diameter (also referred to as an opening diameter). For example, some mask members 3 have an opening diameter of 12 mm or 6 mm.

Figure 16:
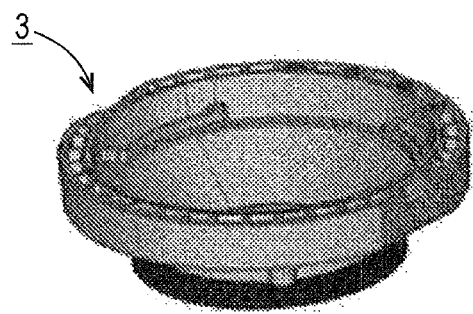
FIG. 16 is a view illustrating the example of the structure of the mask member.
Figure 17:
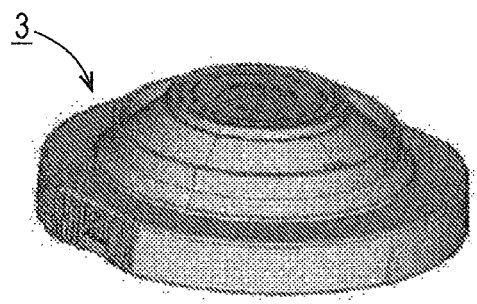
FIG. 17 is a view illustrating an example of a structure of a mask member.
Figure 18:
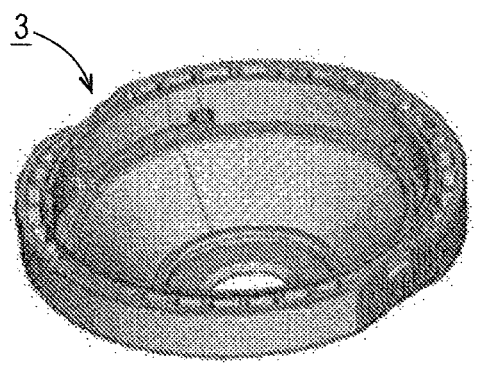
FIG. 18 is a view illustrating the example of the structure of the mask member.
Figure 19:
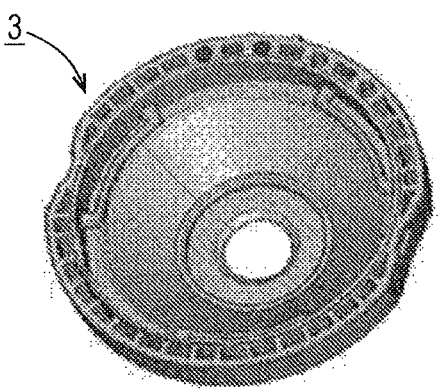
FIG. 19 is a view illustrating an example of a structure of a mask member.
Figure 20:
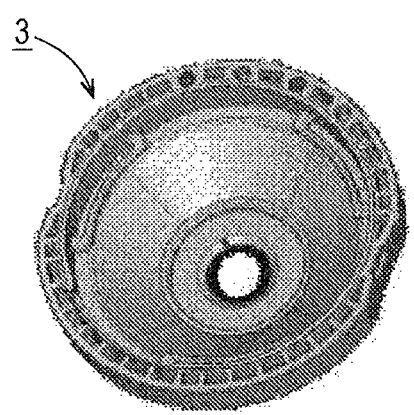
FIG. 20 is a view illustrating the example of the structure of the mask member.

FIGS. 15 to 20 are views illustrating three kinds of mask members 3, for example. FIGS. 15 and 16 illustrate an example of the external appearance of the mask member 3 in which a stabilizing plate with a flat plate shape is provided in a part to be in contact with the color measurement object and the opening protective material is not provided. FIGS. 17 and 18 illustrate an example of the external appearance of the mask member 3 in which a stabilizing plate is not provided in a part to be in contact with the color measurement object and the opening protective material is provided. FIG. 19 illustrates an example of the external appearance of the mask member 3 in which a stabilizing plate is not provided in a part to be in contact with the color measurement object, the opening protective material is not provided, and the opening diameter is 12 mm. FIG. 20 illustrates an example of the external appearance of the mask member in which a stabilizing plate is not provided in a part to be in contact with the color measurement object, the opening protective material is not provided, and the opening diameter is 5 mm.

<(1-6) Flow of Color Measurement Operation>

Figure 21:
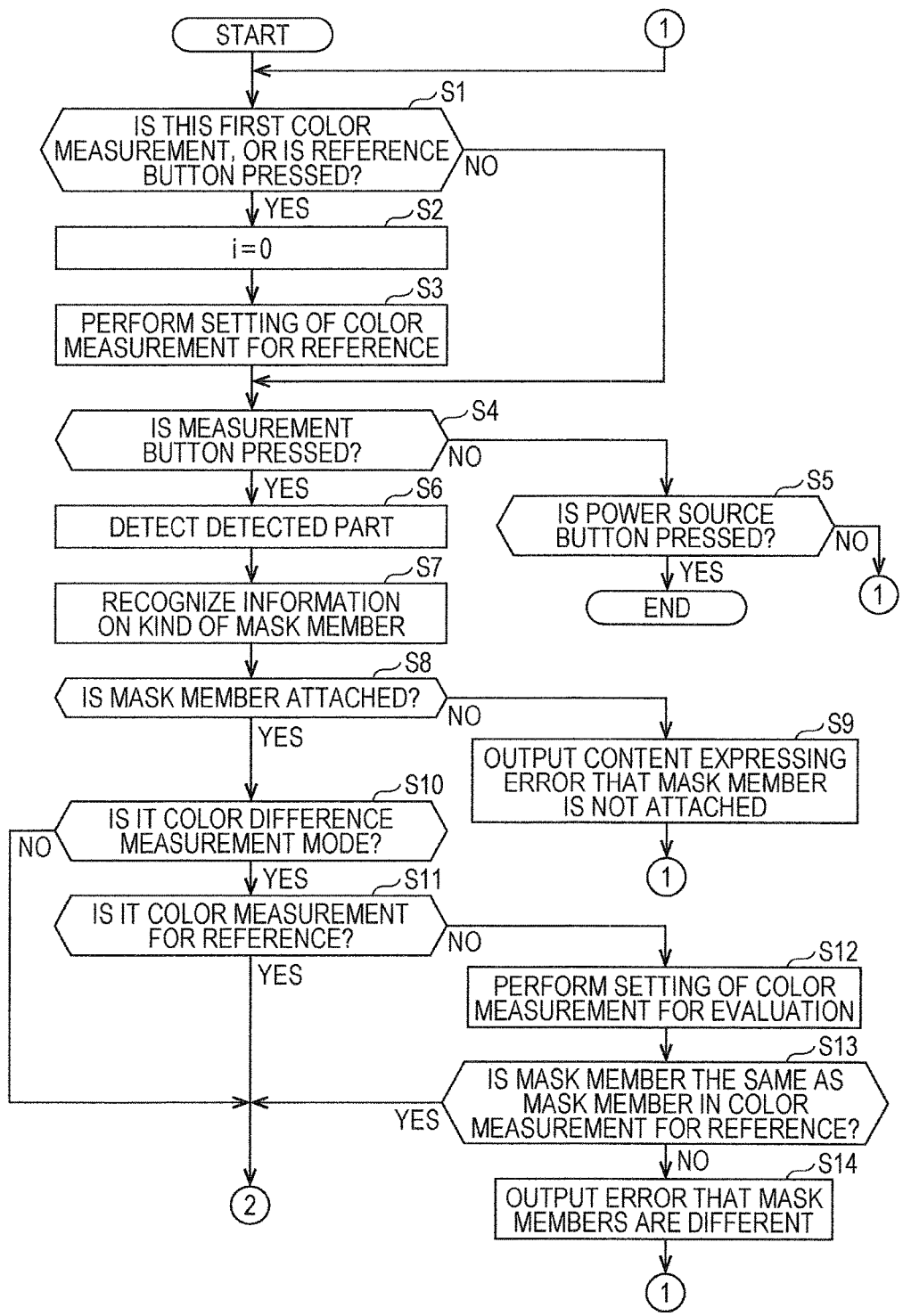
FIG. 21 is a diagram illustrating an example of an operation flow of the color measurement according to one embodiment.
Figure 22:
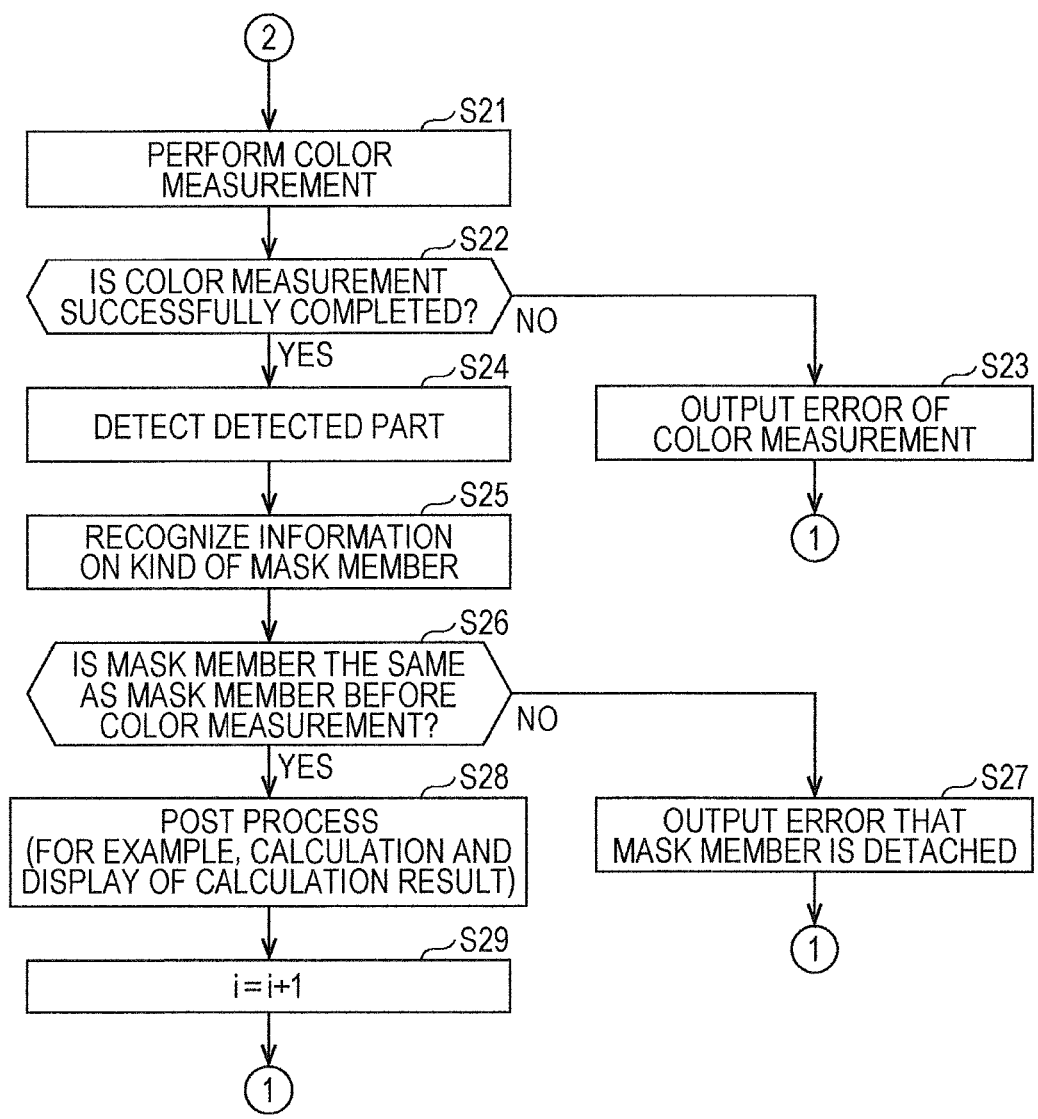
FIG. 22 is a diagram illustrating the operation flow of the color measurement according to one embodiment and one modification.

FIGS. 21 and 22 are diagrams illustrating an example of an operation flow of the color measurement performed by the colorimeter 2. This operation flow is started when the power source button as the fourth input unit 29 is pressed to turn on the power source of the colorimeter 2, and the process advances to step S1.

At the start of this operation flow, for example, the measurement condition may be determined by the user's operation to input the size of the measurement region and the like in the input unit 20, and the content to encourage the user to attach the mask member 3 satisfying the measurement condition may be displayed in the output unit 24. Here, based on the display content in the output unit 24, the user can attach the mask member 3 to the colorimeter 2. In general, when the opening diameter is 8 mm or 12 mm as the size of the measurement region, for example, the content requesting the user to attach the mask member 3 that satisfies the set opening diameter to the colorimeter 2 is displayed.

In step S1 in FIG. 21, the color measurement control unit 210 determines whether this is the first color measurement after the power source is turned on, or whether the reference button is pressed. Here, if this is the first color measurement or the reference button is pressed, the process advances to step S2 and if this is not the first color measurement and the reference button is not pressed, the process advances to step S5.

In step S2, the color measurement control unit 210 sets a numeral i that defines the order of color measurement to 0, and the process advances to step S3. Here, if the numeral i is set to 0, it means that the color measurement for reference is performed.

In step S3, the color measurement control unit 210 performs the setting of the color measurement for reference, and the process advances to step S4.

In step S4, the color measurement control unit 210 determines whether the measurement button is pressed. If the measurement button is not pressed, the process advances to step S5 and if the measurement button is pressed, the process advances to step S6.

In step S5, the control unit 21 determines whether the power source button is pressed. Here, if the power source button is not pressed, the process returns to step S1 and if the power source button is pressed, this operation flow ends and the power source of the colorimeter 2 is turned off.

In step S6, the mask detection unit 25 detects the detected parts 32a to 32d, and the process advances to step S7.

In step S7, the recognition unit 211 recognizes the information on the kind of mask members 3 in accordance with the detection results of the detected parts 32a to 32d by the mask detection unit 25 in step S6. Here, the information on the recognized kind of mask member 3 is, for example, stored in at least one part of a memory, the storage unit 22, and the like.

In step S8, the recognition unit 211 determines whether the mask member 3 is attached to the colorimeter 2. Here, if the mask member 3 is not attached to the colorimeter 2, the process advances to step S9 and if the mask member 3 is attached to the colorimeter 2, the process advances to step S10.

In step S9, the output control unit 217 causes the output unit 24 to output the content expressing an error that the mask member 3 is not attached to the colorimeter 2. For example, the content expressing the error is output visually. Here, when the process in step S9 ends, the process returns to step S1.

In step S10, the control unit 21 determines whether the colorimeter 2 is set to the color difference measurement mode. The color difference measurement mode is a mode in which the color difference between the reference sample and the evaluation object sample is measured. Here, if the colorimeter 2 is not set to the color difference measurement mode, the process advances to step S21 in FIG. 22 and if the colorimeter 2 is set to the color difference measurement mode, the process advances to step S11. Note that this step is necessary when, for example, the colorimeter 2 has other modes than the color difference measurement mode, such as a mode simply measuring the color (also referred to as a color measurement mode). However, for example, if the colorimeter 2 does not have other mode than the color difference measurement mode, this step may be omitted.

In step S11, the color measurement control unit 210 determines whether the setting of the color measurement for reference is performed in step S3. If the setting of the color measurement for reference is not performed, the process advances to step S12 and if the setting of the color measurement for reference is performed, the process advances to step S21 in FIG. 22.

In step S12, the color measurement control unit 210 performs the setting of the color measurement for evaluation, and the process advances to step S13.

In step S13, the color measurement control unit 210 determines whether the mask member 3 attached to the colorimeter 2 is the same as the mask member 3 in the color measurement for reference in accordance with the recognition result in step S7. Here, if the mask member 3 is not the same as the mask member 3 in the color measurement for reference, the process advances to step S14 and if the mask member 3 is the same as the mask member 3 in the color measurement for reference, the process advances to step S21 in FIG. 22.

In step S14, the output control unit 217 causes the output unit 24 to output the content expressing an error that the mask member 3 attached to the colorimeter 2 is not the same as the mask member 3 in the color measurement for reference. For example, the content expressing the error is output visually. Here, when the process of step S14 ends, the process returns to step S1.

In step S21 in FIG. 22, the color measurement of the color measurement object is performed by the light emission control unit 214, the readout unit 215, and the illumination light reception unit 23, and the process advances to step S22. Here, for example, the readout unit 215 reads out the electric signal from the sensor unit 232 having received the light generated from the color measurement object irradiated with the light from the light source unit 231.

In step S22, the color measurement control unit 210 determines whether the color measurement is successfully completed in step S21. If the color measurement is not successfully completed, the process advances to step S23 and if the color measurement is successfully completed, the process advances to step S24. Examples in which the color measurement is not successfully completed include an example in which the mask member 3 is not pressed against the color measurement object as appropriate so that the electric signal obtained from the color measurement in step S21 exhibits an abnormal value.

In step S23, the output control unit 217 causes the output unit 24 to output the content expressing the error that the color measurement is not successfully performed. For example, the content expressing the error is output visually. Here, when the process of step S23 ends, the process returns to step S1 in FIG. 21.

In step S24, the mask detection unit 25 detects the detected parts 32a to 32d, and the process advances to step S25.

In step S25, the recognition unit 211 recognizes the information on the kind of the mask member 3 in accordance with the detection result of the detected parts 32a to 32d by the mask detection unit 25 in step S24. Here, the information on the recognized kind of mask member 3 is, for example, stored in at least one part of the memory, the storage unit 22, and the like.

In step S26, the color measurement control unit 210 determines whether the mask member 3 attached to the colorimeter 2 is the same as the mask member 3 before the color measurement in accordance with the recognition results in Steps S7 and S25. Here, if the mask member 3 attached to the colorimeter 2 is not the same as the mask member 3 before the color measurement, the process advances to step S27 and if the mask member 3 attached to the colorimeter 2 is the same as the mask member 3 before the color measurement, the process advances to step S28.

In step S27, the output control unit 217 causes the output unit 24 to output the content expressing the error that the mask member 3 is detached. For example, the content expressing the error is output visually. Here, when the process of step S27 ends, the process returns to step S1 in FIG. 21.

In step S28, a post process is performed by the calculation unit 216, the output control unit 217, and the comparison unit 218. In this post process, for example, the calculation unit 216 obtains the color measurement result data pertaining to the object color of the color measurement object on the basis of the electric signal read out by the readout unit 215. Here, at the first timing when the color measurement for reference is performed, for example, the output control unit 217 causes the output unit 24 to visually output the color measurement result data obtained in the calculation unit 216 and the data are stored in the storage unit 22. At the second timing when the color measurement for evaluation is performed, for example, the comparison unit 218 calculates the color difference between the color measurement result of the color measurement for reference and the color measurement result of the color measurement for evaluation, and the output control unit 217 causes the output unit 24 to visually output the data expressing the color difference and the data are stored in the storage unit 22.

In step S29, the numeral i that defines the order of the color measurement is increased by one, and the process returns to step S1 in FIG. 21. Note that when the numeral i is n (n is a natural number), for example, it means that the n-th color measurement for evaluation is performed.

<(1-7) Summary of One Embodiment>

As described above, in the colorimeter 2 according to one embodiment, the predetermined output is performed when the mask member 3 in the color measurement for the reference sample and the mask member 3 in the color measurement for the evaluation object sample are not the same. Thus, the discordance of the mask member 3 occurs less between in the color measurement for the reference sample and in the color measurement for the evaluation object sample. As a result, the color difference between the reference sample and the evaluation object sample can be evaluated as appropriate.

(2) Modification

Note that the present invention is not limited to the aforementioned one embodiment and various modifications, improvements, and the like are possible in the range not departing from the concept of the present invention.

For example, in the above one embodiment, the first color measurement after the power source of the colorimeter 2 is turned on and the first color measurement after the reference button is pressed correspond to the color measurement for reference, and this color measurement for reference is followed by the color measurement for evaluation; however, the present invention is not limited to this procedure.

For example, a procedure may be employed in which one or more reference samples are subjected to the color measurement for reference using two or more mask members in order, and then based on one result of the color measurement for reference among the results of the color measurement for reference, the result of the color measurement for evaluation is evaluated. However, in such a usage of the colorimeter, the mask member 3 attached to the colorimeter in the color measurement for reference, which is performed in advance, and the mask member 3 attached to the colorimeter in the color measurement for evaluation are likely to be different. In view of this, a structure may be employed in which a predetermined output is performed in response to the discordance between the information on the kind of the mask member 3 in one combination specified by a specification unit 219 and the information on the kind of the mask member 3 recognized by the recognition unit 211 in accordance with the detection result by the mask detection unit 25 at the second timing. In such a structure, even when the color measurement result data of each of the plurality of reference samples are obtained in advance, the discordance of the mask member 3 occurs less between in the color measurement for the reference sample and in the color measurement for the evaluation object sample. Here, a specific example of this modification is described.

Figure 23:
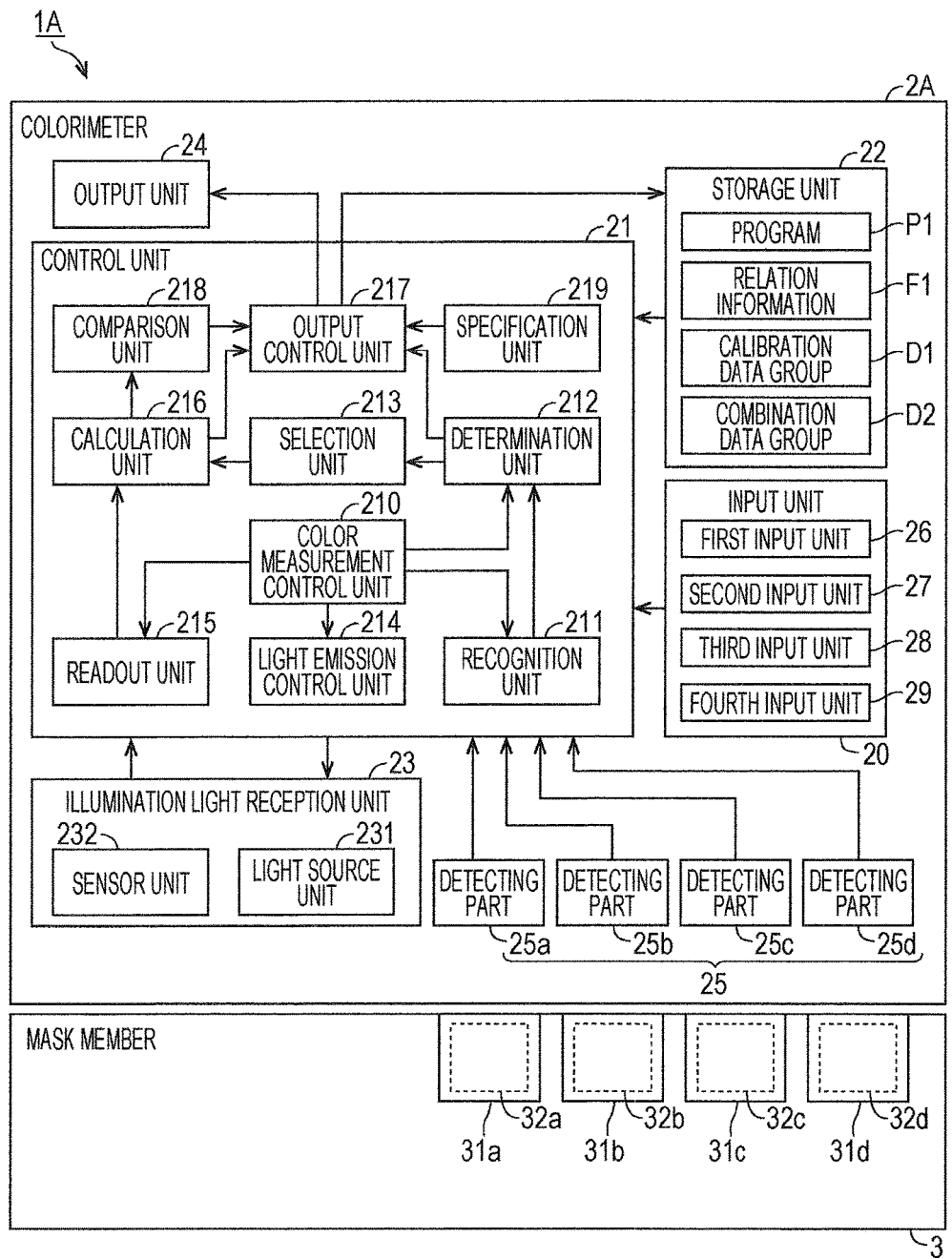
FIG. 23 is a block diagram illustrating an example of functional structures of a color measurement system according to one modification.

FIG. 23 is a diagram illustrating an example of functional structures of a color measurement system 1A according to one modification.

As illustrated in FIG. 23, the color measurement system 1A according to one modification is based on the color measurement system 1 according to one embodiment, and a colorimeter 2A is employed instead of the colorimeter 2. The colorimeter 2A is based on the colorimeter 2 according to the one embodiment, and additionally includes the specification unit 219. Furthermore, in the colorimeter 2A according to the present modification, the storage unit 22 stores a combination data group D2.

The combination data group D2 can be generated by, for example, associating the information on the kind of the mask member recognized by the recognition unit 211 in accordance with the detection result by the mask detection unit 25 and the color measurement result data pertaining to the object color of the reference sample obtained in the calculation unit 216, for each of the plurality of kinds of reference samples. Here, the timing at which the color measurement of the various kinds of reference samples is performed (also referred to as the first timing) includes, for example, at least one timing of: before the color measurement, in the middle of the color measurement, and after the color measurement.

In this mode, for example, at each of the plurality of first timings, one or more detected parts 32a to 32d are detected by the mask detection unit 25 and the color measurement result data are obtained by the illumination light reception unit 23 and the calculation unit 216. Here, for example, the output control unit 217 associates the information on the kind of the mask member recognized by the recognition unit 211 in accordance with the detection result by the mask detection unit 25 and the color measurement result data obtained by the calculation unit 216 for each first timing and these associated information and data are stored in the storage unit 22. Thus, the combination data group D2 can be generated.

The specification unit 219 specifies one combination among the plurality of combinations between the color measurement result data and the information on the kind of the mask member 3 stored in the combination data group D2 stored in the storage unit 22 in accordance with the user operation. Here, for example, in accordance with the operation of the user and in accordance with the signal input from the input unit 20, one combination of the plurality of combinations is specified. One combination specified here is used as the color measurement result of the measurement for reference as the reference based on which comparison with the color measurement result of the subsequent color measurement for evaluation is performed.

In the case where one combination is specified among the plurality of combinations in this manner, the output unit 24 performs a predetermined output at the second timing in response to the discordance between the information on the kind of the mask member 3 in one combination specified by the specification unit 219 and the information on the kind of the mask member 3 recognized by the recognition unit 211 in accordance with the detection result by the mask detection unit 25 at the second timing.

Figure 24:
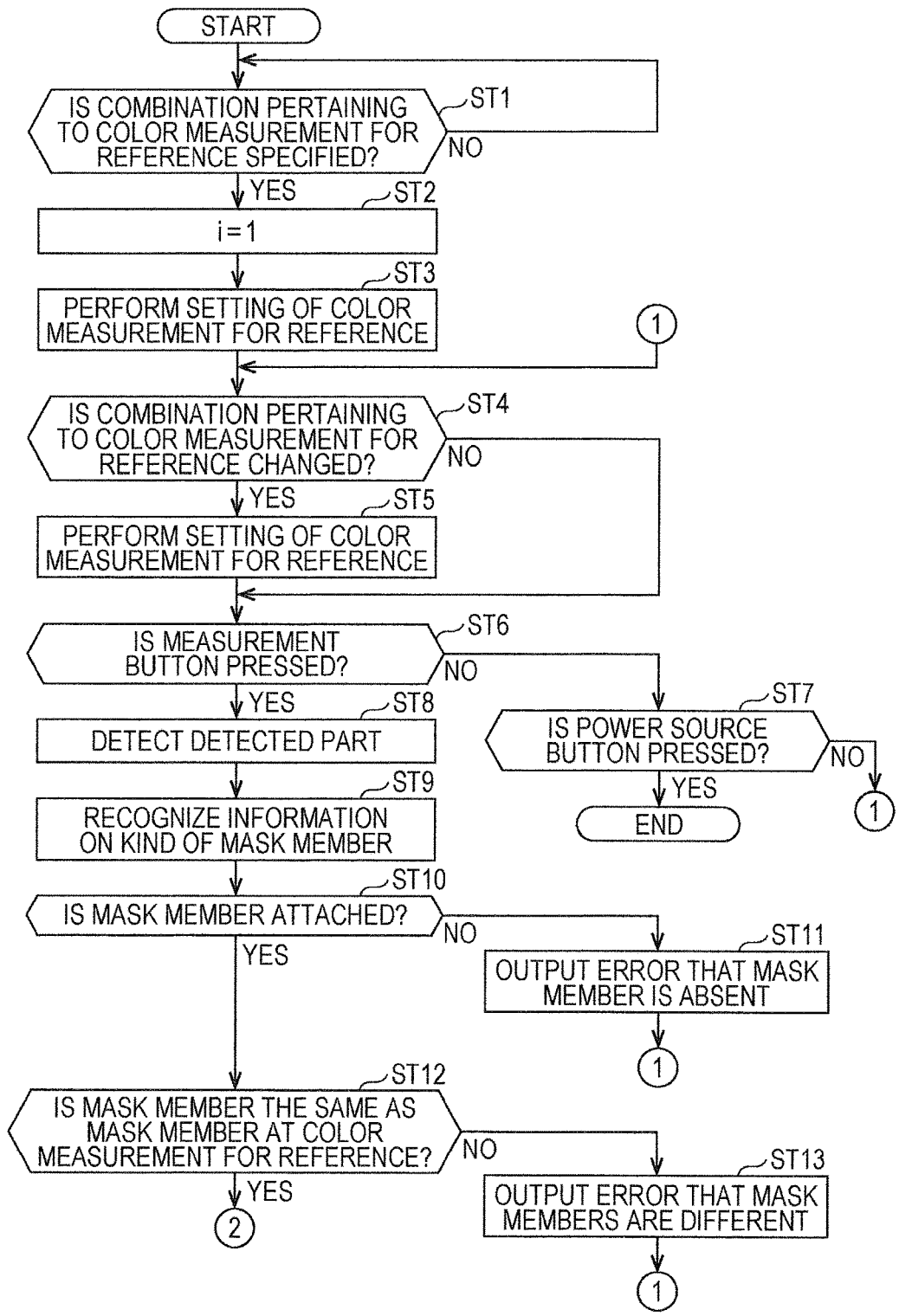
FIG. 24 is a diagram illustrating an example of an operation flow of the color measurement according to one modification.

FIGS. 24 and 22 are diagrams illustrating the operation flow of the color measurement in the colorimeter 2A according to the present modification. This operation flow is started when the power source button as the fourth input unit 29 is pressed to turn on the power source of the colorimeter 2A, and the process advances to step ST1.

In step ST1, the color measurement control unit 210 determines whether the specification unit 219 has specified one combination among the plurality of combinations pertaining to the color measurement for reference included in the combination data group D2. Here, the determination in step ST1 is repeated until one combination among the plurality of combinations is specified, and after one of the combinations is specified, the process is advanced to step ST2.

In step ST2, the color measurement control unit 210 sets the numeral i that defines the order of the color measurement to 1, and the process advances to step ST3. That is to say, if the numeral i is set to 1, it means that the first color measurement for evaluation is performed.

In step ST3, the color measurement control unit 210 performs the setting of the color measurement for reference in accordance with one combination pertaining to the specified color measurement for reference and the process advances to step ST4.

In step ST4, the color measurement control unit 210 determines whether the combination pertaining to the color measurement for reference is changed by the specification unit 219. Here, if one combination specified in the plurality of combinations is changed, the process advances to step ST5 and if one combination specified in the plurality of combinations is not changed, the process advances to step ST6.

In step ST5, the color measurement control unit 210 performs the setting of the color measurement for reference in accordance with one combination pertaining to the color measurement for reference after the change, and the process advances to step ST6.

In step ST6, the color measurement control unit 210 determines whether the measurement button is pressed. Here, if the measurement button is not pressed, the process advances to step ST7, and if the measurement button is pressed, the process advances to step ST8.

In step ST7, the control unit 21 determines whether the power source button is pressed. Here, if the power source button is not pressed, the process returns to step ST4, and if the power source button is pressed, this operation flow ends and the power source of the colorimeter 2A is turned off.

In step ST8, the mask detection unit 25 detects the detected parts 32a to 32d, and the process advances to step ST9.

In step ST9, the recognition unit 211 recognizes the information on the kind of the mask member 3 in accordance with the detection result of the detected parts 32a to 32d by the mask detection unit 25 in step ST8. Here, the information on the recognized kind of the mask member 3 is stored in, for example, at least one part of the memory, the storage unit 22, and the like.

In step ST10, the recognition unit 211 determines whether the mask member 3 is attached to the colorimeter 2A. If the mask member 3 is not attached to the colorimeter 2A, the process advances to step ST11, and if the mask member 3 is attached to the colorimeter 2A, the process advances to step ST12.

In step ST11, the output control unit 217 causes the output unit 24 to output the content expressing the error that the mask member 3 is not attached to the colorimeter 2A. For example, the content expressing the error is output visually. Here, when the process of step ST11 ends, the process returns to step ST4.

In step ST12, the color measurement control unit 210 determines whether the mask member 3 attached to the colorimeter 2A is the same as the mask member 3 in the color measurement for reference in accordance with the recognition result in step ST9. Here, if the mask member 3 is not the same as the mask member 3 in the color measurement for reference, the process advances to step ST13, and if the mask member 3 is the same as the mask member 3 in the color measurement for reference, the process advances to step S21 in FIG. 22. Note that the process from Steps S21 to S28 in FIG. 22 is similar to the process from Steps S21 to S28 according to the one embodiment, and after any process of Steps S23, S27, and S29 ends, the process returns to step ST4 in FIG. 24.

In step ST13, the output control unit 217 causes the output unit 24 to output the content expressing the error that the mask member 3 attached to the colorimeter 2A is not the same as the mask member 3 in the color measurement for reference. For example, the content expressing the error is output visually. Here, when the process of step ST13 ends, the process returns to step ST4.

In the one embodiment and the modification described above, the color difference and the like are calculated by comparing the color measurement result of the color measurement for reference and the color measurement result of the color measurement for evaluation in the comparison unit 218; however, the present invention is not limited to this procedure. For example, the data expressing the color measurement results of the color measurement for reference and the color measurement for evaluation may be transmitted from the output unit 24 to an external device by the output control unit 217 and the external device may calculate the color difference and the like.

In the one embodiment and the modification described above, the recognition unit 211 recognizes the information on the kind of the mask member 3 in accordance with the detection result of one or more detected parts 32a to 32d by the detection unit 25; however, the present invention is not limited to this procedure. For example, the detection unit 25 and the recognition unit 211 may recognize the information on the kind of the mask member 3 by other method including a method using an IC tag.

It is needless to say that the one embodiment and the modification described above may be combined entirely or partly as appropriate within the ranges not contradicting each other.

REFERENCE SIGNS LIST 1, 1A Color measurement system
2, 2A Colorimeter
2WD Window part
2AW Attached part
2BD Casing
3 Mask member
3AT Attaching part
3BD Main body
3WD Window part
20 Input unit
21 Control unit
22 Storage unit
23 Illumination light reception unit
24 Output unit
25 Mask detection unit
25a to 25d First to fourth detecting parts
26 to 29 First to fourth input unit
31a to 31d Mounted part
32a to 32d Detected parts
210 Color measurement control unit
211 Recognition unit
212 Determination unit
213 Selection unit
214 Light emission control unit
215 Readout unit
216 Calculation unit
217 Output unit
218 Comparison unit
219 Specification unit
231 Light source unit
232 Sensor unit
D1 Calibration data group
D2 Combination data group
F1 Relation information
P1 Program

The invention claimed is:

1. A colorimeter comprising:
an illumination light receiver including a light source unit and a sensor;
an attached part where a mask member with a window part is attached so as to cover the illumination light receiver;
a detector that detects one or more detected parts disposed on the mask member attached to the attached part;
a first hardware processor that recognizes information on a kind of the mask member in accordance with a detection result of the one or more detected parts by the detector; and
second hardware processor that causes the first hardware processor to recognize the information on the kind of the mask member in accordance with the detection result by the detector at a first timing, and causes the first hardware processor to recognize the information on the kind of the mask member in accordance with the detection result by the detector at a second timing after the first timing; and
an outputter that performs a predetermined output in response to a discordance between the information on the kind of the mask member recognized by the first hardware processor in accordance with the detection result by the detector at the first timing and the information on the kind of the mask member recognized by the first hardware processor in accordance with the detection result by the detector at the second timing.

2. The colorimeter according to claim 1, wherein
the first timing is a timing at which the colorimeter is set to a reference mode to perform color measurement in which a reference sample to be a reference is an object, and
the second timing is a timing at which the colorimeter is set to a color measurement mode to perform color measurement in which a color measurement object sample different from the reference sample is the object.

3. The colorimeter according to claim 1, wherein
the first timing includes at least one timing of the following: before color measurement, in the middle of color measurement, and after color measurement in the color measurement in which a first sample is an object, and
the second timing includes at least one timing of the following: before color measurement, in the middle of color measurement, and after color measurement in the color measurement in which a second sample different from the first sample is the object.

4. The colorimeter according to claim 3, wherein
the first sample includes a reference sample to be a reference, and
the second sample includes an evaluation object sample as an object whose color difference based on the reference sample is evaluated.

5. The colorimeter according to claim 1, wherein the outputter includes at least one of a display that performs a predetermined visible output, a light emitter that performs predetermined light emission, a projector that performs a predetermined visible output, a speaker that performs a predetermined audible output, and a communicator that outputs a predetermined signal.

6. The colorimeter according to claim 1, wherein the outputter performs an output in a predetermined mode recognizable by a user.

7. The colorimeter according to claim 1, further comprising:
a third hardware processor that obtains color measurement result data pertaining to an object color of the color measurement object on the basis of an electric signal obtained in the illumination light receiver when light from the light source is delivered to the color measurement object and the light generated from the color measurement object is received in the sensor; and
a storage that stores the color measurement result data obtained in the third hardware processor, wherein
the second hardware processor causes the detector to detect the one or more detected parts and causes the illumination light receiver and the third hardware processor to obtain the color measurement result data at each of the plurality of first timings,
the storage stores the information on the kind of the mask member recognized by the first hardware processor in accordance with the detection result by the detector and the color measurement result data obtained by the third hardware processor for each of the plurality of first timings, while associating the information and the data with each other,
the colorimeter further comprises a fourth hardware processor that specifies one combination among a plurality of combinations of the information on the kind of the mask member and the color measurement result data stored in the storage in accordance with a user operation, and
the outputter performs the predetermined output at the second timing in response to a discordance between the information on the kind of the mask member in one combination specified by the fourth hardware processor and the information on the kind of the mask member recognized by the first hardware processor in accordance with the detection result by the detector at the second timing.

8. The colorimeter according to claim 2, wherein the outputter includes at least one of a display that performs a predetermined visible output, a light emitter that performs predetermined light emission, a projector that performs a predetermined visible output, a speaker that performs a predetermined audible output, and a communicator that outputs a predetermined signal.

9. The colorimeter according to claim 2, wherein the outputter performs an output in a predetermined mode recognizable by a user.

10. The colorimeter according to claim 2, further comprising:
a third hardware processor that obtains color measurement result data pertaining to an object color of the color measurement object on the basis of an electric signal obtained in the illumination light receiver when light from the light source is delivered to the color measurement object and the light generated from the color measurement object is received in the sensor; and
a storage that stores the color measurement result data obtained in the third hardware processor, wherein
the second hardware processor causes the detector to detect the one or more detected parts and causes the illumination light receiver and the third hardware processor to obtain the color measurement result data at each of the plurality of first timings,
the storage stores the information on the kind of the mask member recognized by the first hardware processor in accordance with the detection result by the detector and the color measurement result data obtained by the third hardware processor for each of the plurality of first timings, while associating the information and the data with each other,
the colorimeter further comprises a fourth hardware processor that specifies one combination among a plurality of combinations of the information on the kind of the mask member and the color measurement result data stored in the storage in accordance with a user operation, and
the outputter performs the predetermined output at the second timing in response to a discordance between the information on the kind of the mask member in one combination specified by the fourth hardware processor and the information on the kind of the mask member recognized by the first hardware processor in accordance with the detection result by the detector at the second timing.

11. The colorimeter according to claim 3, wherein the outputter includes at least one of a display that performs a predetermined visible output, a light emitter that performs predetermined light emission, a projector that performs a predetermined visible output, a speaker that performs a predetermined audible output, and a communicator that outputs a predetermined signal.

12. The colorimeter according to claim 3, wherein the outputter performs an output in a predetermined mode recognizable by a user.

13. The colorimeter according to claim 3, further comprising:
a third hardware processor that obtains color measurement result data pertaining to an object color of the color measurement object on the basis of an electric signal obtained in the illumination light receiver when light from the light source is delivered to the color measurement object and the light generated from the color measurement object is received in the sensor; and
a storage that stores the color measurement result data obtained in the third hardware processor, wherein
the second hardware processor causes the detector to detect the one or more detected parts and causes the illumination light receiver and the third hardware processor to obtain the color measurement result data at each of the plurality of first timings,
the storage stores the information on the kind of the mask member recognized by the first hardware processor in accordance with the detection result by the detector and the color measurement result data obtained by the third hardware processor for each of the plurality of first timings, while associating the information and the data with each other,
the colorimeter further comprises a fourth hardware processor that specifies one combination among a plurality of combinations of the information on the kind of the mask member and the color measurement result data stored in the storage in accordance with a user operation, and
the outputter performs the predetermined output at the second timing in response to a discordance between the information on the kind of the mask member in one combination specified by the fourth hardware processor and the information on the kind of the mask member recognized by the first hardware processor in accordance with the detection result by the detector at the second timing.

14. The colorimeter according to claim 4, wherein the outputter includes at least one of a display that performs a predetermined visible output, a light emitter that performs predetermined light emission, a projector that performs a predetermined visible output, a speaker that performs a predetermined audible output, and a communicator that outputs a predetermined signal.

15. The colorimeter according to claim 4, wherein the outputter performs an output in a predetermined mode recognizable by a user.

16. The colorimeter according to claim 4, further comprising:
a third hardware processor that obtains color measurement result data pertaining to an object color of the color measurement object on the basis of an electric signal obtained in the illumination light receiver when light from the light source is delivered to the color measurement object and the light generated from the color measurement object is received in the sensor; and
a storage that stores the color measurement result data obtained in the third hardware processor, wherein
the second hardware processor causes the detector to detect the one or more detected parts and causes the illumination light receiver and the third hardware processor to obtain the color measurement result data at each of the plurality of first timings,
the storage stores the information on the kind of the mask member recognized by the first hardware processor in accordance with the detection result by the detector and the color measurement result data obtained by the third hardware processor for each of the plurality of first timings, while associating the information and the data with each other,
the colorimeter further comprises a fourth hardware processor that specifies one combination among a plurality of combinations of the information on the kind of the mask member and the color measurement result data stored in the storage in accordance with a user operation, and
the outputter performs the predetermined output at the second timing in response to a discordance between the information on the kind of the mask member in one combination specified by the fourth hardware processor and the information on the kind of the mask member recognized by the first hardware processor in accordance with the detection result by the detector at the second timing.

17. The colorimeter according to claim 5, further comprising:
a third hardware processor that obtains color measurement result data pertaining to an object color of the color measurement object on the basis of an electric signal obtained in the illumination light receiver when light from the light source is delivered to the color measurement object and the light generated from the color measurement object is received in the sensor; and
a storage that stores the color measurement result data obtained in the third hardware processor, wherein
the second hardware processor causes the detector to detect the one or more detected parts and causes the illumination light receiver and the third hardware processor to obtain the color measurement result data at each of the plurality of first timings,
the storage stores the information on the kind of the mask member recognized by the first hardware processor in accordance with the detection result by the detector and the color measurement result data obtained by the third hardware processor for each of the plurality of first timings, while associating the information and the data with each other,
the colorimeter further comprises a fourth hardware processor that specifies one combination among a plurality of combinations of the information on the kind of the mask member and the color measurement result data stored in the storage in accordance with a user operation, and
the outputter performs the predetermined output at the second timing in response to a discordance between the information on the kind of the mask member in one combination specified by the fourth hardware processor and the information on the kind of the mask member recognized by the first hardware processor in accordance with the detection result by the detector at the second timing.

18. The colorimeter according to claim 6, further comprising:
a third hardware processor that obtains color measurement result data pertaining to an object color of the color measurement object on the basis of an electric signal obtained in the illumination light receiver when light from the light source is delivered to the color measurement object and the light generated from the color measurement object is received in the sensor; and a storage that stores the color measurement result data obtained in the third hardware processor, wherein the second hardware processor causes the detector to detect the one or more detected parts and causes the illumination light receiver and the third hardware processor to obtain the color measurement result data at each of the plurality of first timings, the storage stores the information on the kind of the mask member recognized by the first hardware processor in accordance with the detection result by the detector and the color measurement result data obtained by the third hardware processor for each of the plurality of first timings, while associating the information and the data with each other, the colorimeter further comprises a fourth hardware processor that specifies one combination among a plurality of combinations of the information on the kind of the mask member and the color measurement result data stored in the storage in accordance with a user operation, and the outputter performs the predetermined output at the second timing in response to a discordance between the information on the kind of the mask member in one combination specified by the fourth hardware processor and the information on the kind of the mask member recognized by the first hardware processor in accordance with the detection result by the detector at the second timing.

\* \* \* \* \*